United States Patent
Jodele et al.

(10) Patent No.: US 10,815,296 B2
(45) Date of Patent: Oct. 27, 2020

(54) METHODS OF TREATMENT OF HSCT-ASSOCIATED THROMBOTIC MICROANGIOPATHY WITH ECULIZUMAB

(71) Applicant: Children's Hospital Medical Center, Cincinnati, OH (US)

(72) Inventors: Sonata Jodele, Montgomery, OH (US); Benjamin L. Laskin, Narberth, PA (US)

(73) Assignee: Children's Hospital Medical Center, Cincinnati, OH (US)

( * ) Notice: Subject to any disclaimer, the term of this patent is extended or adjusted under 35 U.S.C. 154(b) by 186 days.

(21) Appl. No.: 14/911,098

(22) PCT Filed: Sep. 16, 2014

(86) PCT No.: PCT/US2014/055922
§ 371 (c)(1),
(2) Date: Feb. 9, 2016

(87) PCT Pub. No.: WO2015/039126
PCT Pub. Date: Mar. 19, 2015

(65) Prior Publication Data
US 2016/0194386 A1    Jul. 7, 2016

Related U.S. Application Data

(60) Provisional application No. 61/878,119, filed on Sep. 16, 2013.

(51) Int. Cl.
*A61K 39/395* (2006.01)
*C07K 16/18* (2006.01)
*G01N 33/68* (2006.01)
*G01N 33/94* (2006.01)
*A61K 39/00* (2006.01)

(52) U.S. Cl.
CPC ......... *C07K 16/18* (2013.01); *G01N 33/6893* (2013.01); *G01N 33/94* (2013.01); *A61K 2039/505* (2013.01); *C07K 2317/24* (2013.01); *C07K 2317/76* (2013.01); *C07K 2317/94* (2013.01); *G01N 2333/4716* (2013.01); *G01N 2800/226* (2013.01); *G01N 2800/52* (2013.01)

(58) Field of Classification Search
None
See application file for complete search history.

(56) References Cited

U.S. PATENT DOCUMENTS

| 9,494,601 B2 | 11/2016 | McKnight et al. |
| 2006/0234285 A1 | 10/2006 | Gentz et al. |
| 2007/0116710 A1 | 5/2007 | Bell et al. |
| 2009/0269356 A1* | 10/2009 | Epstein ............ C12N 15/115 514/1.1 |
| 2011/0212900 A1 | 9/2011 | Ikezoe et al. |
| 2012/0225056 A1 | 9/2012 | Rother et al. |
| 2015/0050671 A1 | 2/2015 | Wippermann et al. |
| 2015/0174243 A1 | 6/2015 | Magro |
| 2016/0046709 A1 | 2/2016 | Welcher et al. |

FOREIGN PATENT DOCUMENTS

| WO | WO 2004/034988 A2 | 4/2004 |
| WO | WO 2014/003744 A1 | 1/2014 |
| WO | WO 2015/039126 A1 | 3/2015 |
| WO | WO 2015/070041 A1 | 5/2015 |
| WO | WO 2016/200627 A1 | 12/2016 |

OTHER PUBLICATIONS

Written Opinion of the International Searching Authority of PCT /US14/55922 (dated Mar. 19, 2015).*
International Search Report and Written Opinion dated Sep. 9, 2016 for Application No. PCT/US2016/034547, 10 pgs.
Jodele, S., et al., "A new paradigm: Diagnosis and management of HSCT-associated thrombotic microangiopathy as multi-system endothelial injury," Blood Rev. May 2015,29(3):191-204, 37 pgs.
Jodele, S., et al., "Variable eculizumab clearance requires pharmacodynamic monitoring to optimize therapy for thrombotic microangiopathy after hemotopoietic stem cell transplantation," Biol Blood Marrow Transplant, Feb. 2016, 22(2):307-315, 29 pgs.
Canadian Office Action dated Jan. 25, 2017 for Application No. CA 2,921,856, 4 pgs.
De Fontbrune, F.S., et al., "Use of Eculizumab in Patients with Allogeneic Stem Cell Transplant-Associated Thrombotic Microangiopathy: A Study from the SFGM-TC," Transplantation, Sep. 2015, 99(9):1953-1959, XP55331429, 7 pgs.
George, J.N., et al., "Thrombotic microangiopathy after allogeneic bone marrow transplantation: a pathologic abnormality associated with diverse clinical syndromes," Bone Marrow Transplantation, Jun. 2004: 33(11):1073-1074, XP055352969, 2 pgs.
Extended European Search Report and Opinion dated Mar. 20, 2017 for Application No. EP 14843902.9, 9 pgs.
Canadian Office Action dated Feb. 8, 2018 for Application No. CA 2,921,856, 4 pgs.
Aldoss O, et al., "Pericardial effusion after pediatric hematopoietic cell transplant," Pediatr Transplant, 2013;17:294-9, 6 pgs.
Aljitawi OS, et al., "Late-onset intestinal perforation in the setting of posttransplantation microangiopathy: a case report," Transplant Proc, 2010; 42:3892-3, 2 pgs.

(Continued)

*Primary Examiner* — Phillip Gambel
(74) *Attorney, Agent, or Firm* — Frost Brown Todd LLC; Nicole M. Tepe

(57) ABSTRACT

Disclosed are drugs capable of inhibiting the complement pathway for use for treating hematopoietic stem cell transplant (HSCT) associated thrombotic microangiopathy (HSCT-TMA, also called TA-TMA) in a subject that has undergone an HSCT. Also disclosed are methods of using drugs capable of inhibiting the complement pathway for use for treating hematopoietic stem cell transplant (HSCT) associated thrombotic microangiopathy (HSCT-TMA) in a subject that has undergone an HSCT.

17 Claims, 7 Drawing Sheets

(56) References Cited

OTHER PUBLICATIONS

Arai Y, et al., "Serum neutrophil extracellular trap levels predict thrombotic microangiopathy after allogeneic stem cell transplantation," Biol Blood Marrow Transplant, 2013; 19:1683-9, 7 pgs.
Au W-Y, et al., "Successful treatment of thrombotic microangiopathy after haematopoietic stem cell transplantation with rituximab," Br J Haematol, 2007; 137:475-8, 4 pgs.
Batts ED, et al., "Diagnosis and treatment of transplantation-associated thrombotic microangiopathy: real progress or are we still waiting?" Bone Marrow Transplant, 2007; 40:709-19, 11 pgs.
Biedermann BC., "Vascular endothelium and graft-versus-host disease," Best Pract Res Clin Haematol, 2008; 21:129-38, 10 pgs.
Brukamp K, et al., "Nephrotic syndrome after hematopoietic cell transplantation: do glomerular lesions represent renal graft-versus-host disease?" Clin J Am Soc Nephrol, 2006; 1:685-94, 10 pgs.
Carella AM, et al., "Rituximab for allo-SCT-associated thrombotic thrombocytopenic purpura," Bone Marrow Transplant, 2008; 41:1063-5, 3 pgs.
Carmona A, et al., "Distinct deleterious effects of cyclosporine and tacrolimus and combined tacrolimus-sirolimus on endothelial cells: protective effect of defibrotide," Biol Blood Marrow Transplant, 2013; 19:1439-45, 7 pgs.
Carreras E, et al., "The role of the endothelium in the short-term complications of hematopoietic SCT," Bone Marrow Transplant, 2011; 46:1495-502, 8 pgs.
Cataland SR, et al., "Biomarkers of the alternative pathway and terminal complement activity at presentation confirms the clinical diagnosis of aHUS and differentiates aHUS from TTP," Blood, Jun. 12, 2014; 123(24):3733-8, 7 pgs.
Chalandon Y, et al., "Prevention of veno-occlusive disease with defibrotide after allogeneic stem cell transplantation," Biol Blood Marrow Transplant, 2004; 10:347-54, 8 pgs.
Chang A, et al., "Spectrum of renal pathology in hematopoietic cell transplantation: a series of 20 patients and review of the literature," Clin J Am Soc Nephrol, 2007; 2:1014-23, 10 pgs.
Changsirikulchai S, et al., "Renal thrombotic microangiopathy after hematopoietic cell transplant: role of GVHD in pathogenesis," Clin J Am Soc Nephrol, 2009; 4:345-53, 9 pgs.
Cho BS, et al., "Clinical impact of thrombotic microangiopathy on the outcome of patients with acute graft-versus-host disease after allogeneic hematopoietic stem cell transplantation," Bone Marrow Transplant, 2008; 41:813-20, 8 pgs.
Cho BS, et al., "Validation of recently proposed consensus criteria for thrombotic microangiopathy after allogeneic hematopoietic stem-cell transplantation," Transplantation, 2010; 90:918-26, Abstract Only, 1 pg.
Choi CM, et al., "Thrombotic microangiopathy in haematopoietic stem cell transplantation: diagnosis and treatment," Drugs, 2009; 69:183-98, 17 pgs.
Colvin RB., "Antibody-mediated renal allograft rejection: diagnosis and pathogenesis," J Am Soc Nephrol, 2007; 18:1046-56, 11 pgs.
Cooke KR, et al., "The contribution of endothelial activation and injury to end-organ toxicity following allogeneic hematopoietic stem cell transplantation," Biol Blood Marrow Transplant, 2008; 14:23-32, 10 pgs.
Corbacioglu S, et al., "Defibrotide for prophylaxis of hepatic veno-occlusive disease in paediatric haemopoietic stem-cell transplantation: an open-label, phase 3, randomised controlled trial," Lancet, 2012; 379:1301-9, 9 pgs.
Crovetto F, et al., "The genetics of the alternative pathway of complement in the pathogenesis of HELLP syndrome," The Journal of Maternal-Fetal & Neonatal Medicine: The Official Journal of the European Association of Perinatal Medicine, the Federation of Asia and Oceania Perinatal Societies, the International Society of Perinatal Obstet, 2012; 25:2322-5, 5 pgs.
Cutler C, et al., "Sirolimus and thrombotic microangiopathy after allogeneic hematopoietic stem cell transplantation," Biol Blood Marrow Transplant, 2005; 11:551-7, 7 pgs.

Dandoy CE, et al., "Pulmonary hypertension after hematopoietic stem cell transplantation," Biol Blood Marrow Transplant, 2013; 19:1546-56, 11 pgs.
Dierickx D, et al., "Thrombotic microangiopathy following intestinal transplantation: a single center experience," Transplant Proc, 2010; 42:79-81, 3 pgs.
Eremina V, et al., "VEGF inhibition and renal thrombotic microangiopathy," N Engl J Med, 2008; 358:1129-36, 12 pgs.
Falkner B, et al., Summary of the fourth report on the Diagnosis, Evaluation, and Treatment of High Blood Pressure in Children and Adolescents, Hypertension, 2004; 44:387-388, 2 pgs.
Fuge R, et al., "The clinical features, risk factors and outcome of thrombotic thrombocytopenic purpura occurring after bone marrow transplantation," Br J Haematol, 2001; 113:58-64, 7 pgs.
Fujino M, et al., "Intestinal thrombotic microangiopathy induced by FK506 in rats," Bone Marrow Transplant, 2007; 39:367-72, 6 pgs.
Galie N, et al., "Guidelines for the Diagnosis and Treatment of Pulmonary Hypertension: The Task Force for the Diagnosis and Treatment of Pulmonary Hypertension of the European Society of Cardiology (ESC) and the European Respiratory Society (ERS), endorsed by the International Society of Heart and Lung Transplantation (ISHLT)," European Heart Journal, 2009; 30:2493-537, 45 pgs.
George JN, et al., "Thrombotic thrombocytopenic purpura-hemolytic uremic syndrome following allogeneic HPC transplantation: a diagnostic dilemma," Transfusion, 2004; 44:294-304, 11 pgs.
Glezerman IG, et al., "Chronic kidney disease, thrombotic microangiopathy, and hypertension following T cell-depleted hematopoietic stem cell transplantation," Biol Blood Marrow Transplant, 2010; 16:976-84, 9 pgs.
Goodwin JE, et al., "Glucocorticoid-induced hypertension," Pediatr Nephrol, 2012; 27:1059-66, Abstract Only, 1 pg.
Gooley TA, et al., "Reduced mortality after allogeneic hematopoietic-cell transplantation," N Engl J Med, 2010; 363:2091-101, 11 pgs.
Haines HL, et al., "Blood, and not urine, BK viral load predicts renal outcome in children with hemorrhagic cystitis following hematopoietic stem cell transplantation," Biol Blood Marrow Transplant, 2011; 17:1512-9, 8 pgs.
Hale GA, et al., "Hemolytic uremic syndrome after bone marrow transplantation: clinical characteristics and outcome in children," Biol Blood Marrow Transplant, 2005; 11:912-20, 9 pgs.
Hewamana S, et al., "Intestinal perforation secondary to haematopoietic stem cell transplant associated thrombotic microangiopathy," Eur J Haematol, 2009; 83:277, 1 pg.
Hingorani S, et al., "Urinary cytokines after HCT: evidence for renal inflammation in the pathogenesis of proteinuria and kidney disease," Bone Marrow Transplant, 2014; 49:403-9, 7 pgs.
Hingorani S., "Chronic kidney disease after liver, cardiac, lung, heart-lung, and hematopoietic stem cell transplant," Pediatr Nephrol, 2008; 23:879-88, 10 pgs.
Hingorani SR, et al., "Albuminuria in hematopoietic cell transplantation patients: prevalence, clinical associations, and impact on survival," Biol Blood Marrow Transplant 2008; 14:1365-72, 8 pgs.
Ho VT, et al., "Blood and marrow transplant clinical trials network toxicity committee consensus summary: thrombotic microangiopathy after hematopoietic stem cell transplantation," Biol Blood Marrow Transplant, 2005; 11:571-5, 5 pgs.
Hoffmeister PA, et al., "Hypertension in long-term survivors of pediatric hematopoietic cell transplantation," Biol Blood Marrow Transplant, 2010; 16:515-24, 10 pgs.
Holmes LV, et al., "Determining the population frequency of the CFHR3/CFHR1 deletion at 1q32," PloS one, 2013; 8:e60352, 7 pgs.
Houtchens J, et al., "Diagnosis and management of pulmonary arterial hypertension," Pulmonary medicine, 2011; 2011:845-864, 14 pgs.
Imhof BA, Aurrand-Lions M. Angiogenesis and inflammation face off Nature medicine. 2006;12:171-2, 2 pgs.
Inamoto Y, et al., "Clinicopathological manifestations and treatment of intestinal transplant-associated microangiopathy," Bone Marrow Transplant, 2009; 44:43-9, 7 pgs.
Inker LA, et al., "Estimating glomerular filtration rate from serum creatinine and cystatin C," N Engl J Med, 2012; 367:20-9, 15 pgs.

(56) References Cited

OTHER PUBLICATIONS

Ishikawa Y, et al., "Transplantation-associated thrombotic microangiopathy after steroid pulse therapy for polyserositis related to graft-versus-host disease," Clin Exp Nephrol, 2011; 15:179-83, Abstract Only, 1 pg.
Jodele S, et al., "Abnormalities in the alternative pathway of complement in children with hematopoietic stem cell transplant-associated thrombotic microangiopathy," Blood. 2013; 122:2003-7, 6 pgs.
Jodele S, et al., "Does early initiation of therapeutic plasma exchange improve outcome in pediatric stem cell transplant-associated thrombotic microangiopathy?" Transfusion, 2013; 53:661-7, 8 pgs.
Jodele S, et al., "Eculizumab Therapy in Children with Severe Hematopoietic Stem Cell Transplantation-Associated Thrombotic Microangiopathy," Biol Blood Marrow Transplant, Apr. 2013; 20(4):518-25, 8 pgs.
Jodele S, et al., "Pulmonary arterial hypertension in pediatric patients with hematopoietic stem cell transplant-associated thrombotic microangiopathy," Biol Blood Marrow Transplant, 2013; 19:202-7, 6 pgs.
Jodele S, et al., "Refined diagnostic and risk criteria for HSCT-associated thrombotic microangiopathy: a prospective study in children and young adults," Blood, Jul. 24, 2014;124(4):645-53, 10 pgs.
Jodele S, et al., "Successful early intervention for hyperacute transplant-associated thrombotic microangiopathy following pediatric hematopoietic stem cell transplantation," Pediatr Transplant, 2012; 16:E39-42, 4 pgs.
Keir L, et al., "Advances in our understanding of the pathogenesis of glomerular thrombotic microangiopathy," Pediatr Nephrol, 2011; 26:523-33, 11 pgs.
Kersting S, et al., "Acute renal failure after allogeneic myeloablative stem cell transplantation: retrospective analysis of incidence, risk factors and survival," Bone Marrow Transplant, 2007; 39:359-65, 7 pgs.
Kielstein JT, et al., "Best supportive care and therapeutic plasma exchange with or without eculizumab in Shiga-toxin-producing E. coli O104:H4 induced haemolytic-uraemic syndrome: an analysis of the German STEC-HUS registry," Nephrol Dial Transplant, 2012; 27:3807-15, 9 pgs.
Kojouri K, et al., "Thrombotic microangiopathy following allogeneic hematopoietic stem cell transplantation," Curr Opin Oncol, 2007; 19:148-54, 7 pgs.
Kurniati NF, et al., "Pleiotropic effects of angiopoietin-2 deficiency do not protect mice against endotoxin-induced acute kidney injury," Nephrol Dial Transplant, 2013; 28:567-75, 9 pgs.
Labrador J, et al., "Risk factors for thrombotic microangiopathy in allogeneic hematopoietic stem cell recipients receiving GVHD prophylaxis with tacrolimus plus MTX or sirolimus," Bone Marrow Transplant, May 2014; 49(5):684-90, 7 pgs.
Lapeyraque AL, et al., "Eculizumab in severe Shiga-toxin-associated HUS," N Engl J Med, 2011; 364:2561-3, 3 pgs.
Laskin BL, et al., "Cystatin C-estimated glomerular filtration rate in pediatric autologous hematopoietic stem cell transplantation," Biol Blood Marrow Transplant, 2012; 18:1745-52, 8 pgs.
Laskin BL, et al., "Early clinical indicators of transplant-associated thrombotic microangiopathy in pediatric neuroblastoma patients undergoing auto-SCT," Bone Marrow Transplant, 2011; 46:682-9, 8 pgs.
Laskin BL, et al., "Renal Arteriolar C4d Deposition: A Novel Characteristic of Hematopoietic Stem Cell Transplantation-Associated Thrombotic Microangiopathy," Transplantation, Jul. 27, 2013; 96(2):217-23, Abstract Only, 1 pg.
Laskin BL, et al., "Small vessels, big trouble in the kidneys and beyond: hematopoietic stem cell transplantation-associated thrombotic microangiopathy," Blood. 2011; 118:1452-62, 12 pgs.
Latour, et al., "Successful use of eculizumab in a patient with post-transplant thrombotic microangiopathy," Br J Haematol, Jan. 7, 2013; 161:279-298, 2 pgs.

Legendre CM, et al., "Eculizumab in atypical hemolytic-uremic syndrome," N Engl J Med, 2013; 369:1379-80, 4 pgs.
Lerner D, et al., "Pericardial effusion in pediatric SCT recipients with thrombotic microangiopathy," Bone Marrow Transplant, Jun. 2014; 49(6):862-3, 2 pgs.
Licht C, et al., "Successful plasma therapy for atypical hemolytic uremic syndrome caused by factor H deficiency owing to a novel mutation in the complement cofactor protein domain 15," Am J Kidney Dis, 2005; 45:415-21, 7 pgs.
Lopes Da Silva R, et al., "BK virus encephalitis with thrombotic microangiopathy in an allogeneic hematopoietic stem cell transplant recipient," Transpl Infect Dis. 2011; 13:161-7, 8 pgs.
Lovric S, et al., "Removal of elevated circulating angiopoietin-2 by plasma exchange—a pilot study in critically ill patients with thrombotic microangiopathy and anti-glomerular basement membrane disease," Thrombosis and Haemostasis, 2010; 104:1038-43, 6 pgs.
Marr H, et al., "Successful treatment of transplant-associated microangiopathy with rituximab," N Z Med J, 2009; 122:72-4, 3 pgs.
Martinez MT, et al., "Transplant-associated microangiopathy (TAM) in recipients of allogeneic hematopoietic stem cell transplants," Bone Marrow Transplant, 2005; 36:993-1000, 8 pgs.
Menne J, et al., "Validation of treatment strategies for enterohaemorrhagic Escherichia coli O104:H4 induced haemolytic uraemic syndrome: case-control study," BMJ, 2012; 345:e4565, 13 pgs.
Mii A, et al. "Renal thrombotic microangiopathy associated with chronic humoral graft versus host disease after hematopoietic stem cell transplantation," Pathol Int, 2011; 61:34-41, 8 pgs.
Mii A, et al., "Renal thrombotic microangiopathy associated with chronic graft-versus-host disease after allogeneic hematopoietic stem cell transplantation," Pathol Int, 2011; 61:518-27, 10 pgs.
Milan A, et al., "Echocardiographic indexes for the non-invasive evaluation of pulmonary hemodynamics," Journal of the American Society of Echocardiography: Official Publication of the American Society of Echocardiography, 2010; 23:225-39; quiz 332-4, 15 pgs.
Mohammed J, et al., "Cardiac tamponade in diarrhoea-positive haemolytic uraemic syndrome," Nephrol Dial Transplant, 2009; 24:679-81, 3 pgs.
Moulder JE, et al., "Captopril and losartan for mitigation of renal injury caused by single-dose total-body irradiation," Radiation Research, 2011; 175:29-36, 8 pgs.
Nadasdy T., "Thrombotic microangiopathy in renal allografts: the diagnostic challenge," Current opinion in organ transplantation, 2014; 19:283-92, Abstract Only, 1 pg.
Naina HV, et al., "Thrombotic microangiopathy during peripheral blood stem cell mobilization," J Clin Apher, 2009; 24:259-61, 3 pgs.
Nakamae H, et al., "Risk factor analysis for thrombotic microangiopathy after reduced-intensity or myeloablative allogeneic hematopoietic stem cell transplantation," Am J Hematol, 2006; 81:525-31, 7 pgs.
Nakamura Y, et al., "Nephrotic syndrome associated with thrombotic microangiopathy following allogeneic stem-cell transplantation for myelodysplastic syndrome," Br J Haematol, 2007; 136:857-9; author reply 9-60, 3 pgs.
Narimatsu H, et al., "Intestinal thrombotic microangiopathy following reduced-intensity umbilical cord blood transplantation," Bone Marrow Transplant, 2005; 36:517-23, 7 pgs.
Nehus EJ, et al., "Performance of cystatin C-based equations in a pediatric cohort at high risk of kidney injury," Pediatr Nephrol, 2013; 28:453-61, Abstract Only, 1 pg.
Nishida T, et al., "Intestinal thrombotic microangiopathy after allogeneic bone marrow transplantation: A clinical imitator of acute enteric graft-versus-host disease," Marrow Transplant, 2004; 33:1143-50, 8 pgs.
Noris M, et al., "Atypical hemolytic-uremic syndrome," N Engl J Med, 2009; 361:1676-87, 12 pgs.
Noris M, et al., "STEC-HUS, atypical HUS and TTP are all diseases of complement activation" Nature reviews Nephrology, 2012; 8:622-33, 12 pgs.
Norkin M, et al., "Large pericardial effusion as a complication in adults undergoing SCT" Bone Marrow Transplant, 2011; 46:1353-6, 4 pgs.

(56) References Cited

OTHER PUBLICATIONS

O'Donnell PH, et al., "BK virus infectien is associated with hematuria and renal impairment in recipients of allogeneic hematopoetic stem cell transplants," Biol Blood Marrow Transplant, 2009; 15:1038-48 e1, 12 pgs.

Orth D, et al., "Shiga toxin activates complement and binds factor H: evidence for an active role of complement in hemolytic uremic syndrome," J Immunol, 2009; 182:6394-400, 7 pgs.

Parikh CR, et al., "Acute renal failure independently predicts mortality after myeloablative allogeneic hematopoietic cell transplant," Kidney Int, 2005; 67: 1999-2005, 8 pgs.

Perkowska-Ptasinska A, et al., "Thrombotic nephropathy and pulmonary hypertension following autologous bone marrow transplantation in a patient with acute lymphoblastic leukemia: case report," Transplant Proc, 2006; 38:295-6, 2 pgs.

Peyvandi F, et al., "Prospective study on the behaviour of the metalloprotease ADAMTS13 and of von Willebrand factor after bone marrow transplantation," Br J Haematol, 2006; 134:187-95, 9 pgs.

Piscitelli D, et al., "Unusual case report of thrombotic microangiopathy of the small bowel following liver transplantation, a possible immunosuppressant-induced disease with histological and ultrastructural findings," TheScientificWorldJournal. 2009; 9:1031-4, 5 pgs.

Platzbecker U, et al., "Graft-versus-host disease prophylaxis with everolimus and tacrolimus is associated with a high incidence of sinusoidal obstruction syndrome and microangiopathy: results of the EVTAC trial," Biol Blood Marrow Transplant, 2009; 15:101-8, 8 pgs.

Rabinovich M., "Molecular pathogenesis of pulmonary arterial hypertension," The Journal of clinical investigation 2012; 122:4306-13, 9 pgs.

Rajpal JS, et al., "Improved survival over the last decade in pediatric patients requiring dialysis after hematopoietic cell transplantation," Biol Blood Marrow Transplant, 2013;19:661-5, 5 pgs.

Reti M, et al., "Complement activation in thrombotic thrombocytopenic purpura," Journal of Thrombosis and Haemostasis: JTH, 2012; 10:791-8, 8 pgs.

Richardson PG, et al., "Defibrotide for the treatment of severe hepatic veno-occlusive disease and multiorgan failure after stem cell transplantation: a multicenter, randomized, dose-finding trial," Biol Blood Marrow Transplant, 2010; 16: 1005-17, 13 pgs.

Rodriguez R, et al., "A phase II pilot study of tacrolimus/sirolimus GVHD prophylaxis for sibling donor hematopoietic stem cell transplantation using 3 conditioning regimens," Blood, 2010; 115:1098-105, 9 pgs.

Rosenthal J, et al., "Transplant-associated thrombotic microangiopathy in pediatric patients treated with sirolimus and tacrolimus," Pediatr Blood Cancer, 2011; 57:142-6, 10 pgs.

Roth C, et al., "The posterior reversible encephalopathy syndrome: what's certain, what's new?" Practical Neurology, 2011; 11:136-44, Abstract Only, 1 pg.

Ruutu T, et al., "Diagnostic criteria for hematopoietic stem cell transplant-associated microangiopathy: results of a consensus process by an International Working Group," Haematologica, 2007; 92:95-100, 6 pgs.

Sadeghi B, et al., "Early-phase GVHD gene expression profile in target versus non-target tissues: kidney, a possible target?" Bone Marrow Transplant, 2013; 48:284-93, 10 pgs.

Sagrista-Sauleda J, et al., "Diagnosis and management of pericardial effusion," World Journal of Cardiology, 2011; 3:135-43, 9 pgs.

San T, et al., "Protective effect of defibrotide on perfusion induced endothelial damage," Thrombosis research, 2000; 99:335-41, 7 pgs.

Schroder H., "Defibrotide protects endothelial cells, but not L929 tumour cells, from tumour necrosis factor-alpha-mediated cytotoxicity," The Journal of Pharmacy and Pharmacology, 1995; 47:250-2, Abstract Only, 1 pg.

Schwartz GJ, et al., "Glomerular filtration rate measurement and estimation in chronic kidney disease," Pediatr Nephrol, 2007; 22:1839-48, 10 pgs.

Schwimmer J, et al., "De novo thrombotic microangiopathy in renal transplant recipients: a comparison of hemolytic uremic syndrome with localized renal thrombotic microangiopathy," Am J Kidney Dis, 2003; 41:471-9, 9 pgs.

Shayani S, et al., "Thrombotic microangiopathy associated with sirolimus level after allogeneic hematopoietic cell transplantation with tacrolimus/sirolimus-based graft-versus-host disease prophylaxis," Biol Blood Marrow Transplant, 2013; 19:298-304, 7 pgs.

Siami K, et al., "Thrombotic microangiopathy after allogeneic hematopoietic stem cell transplantation: an autopsy study," Transplantation, 2008; 85:22-8, 7 pgs.

Song D, et al., "The spectrum of renal thrombotic microangiopathy in lupus nephritis," Arthritis Research & Therapy, 2013; 15:R12, 12 pgs.

Spector, et al., "Associations of blood lead with estimated glomerular filtration rate using MDRD, CKD-EPI and serum cystatin C-based equations," Nephrol Dial Transplant, Jan. 19, 2011, 26:2786-2792, 8 pgs.

Staykov D, et al., "Posterior reversible encephalopathy syndrome," Journal of Intensive Care Medicine, 2012; 27:11-24, Abstract Only, 1 pg.

Sucak GT, et al., "Treatment of sinusoidal obstruction syndrome with defibrotide: a single-center experience," Transplant Proc, 2007; 39:1558-63, 6 pgs.

Takatsuka H, et al., "Complications after bone marrow transplantation are manifestations of systemic inflammatory response syndrome," Bone Marrow Transplant, 2000; 26:419-26, 9 pgs.

Tati R, et al., "Complement activation associated with ADAMTS13 deficiency in human and murine thrombotic microangiopathy," J Immunol, 2013; 191:2184-93, 11 pgs.

Thurman JM, et al., "Alternative pathway of complement in children with diarrhea-associated hemolytic uremic syndrome," Clin J Am Soc Nephrol, 2009; 4:1920-4, 5 pgs.

Tichelli A, et al., "Vascular endothelium as 'novel' target of graft-versus-host disease," Best Pract Res Clin Haematol, 2008; 21:139-48, 10 pgs.

Totina A, et al., "Atypical hemolytic-uremic syndrome in a child presenting with malignant hypertension," Clinical pediatrics, 2013; 52:183-6, 5 pgs.

Tsai HM., "Untying the knot of thrombotic thrombocytopenic purpura and atypical hemolytic uremic syndrome," Am J Med, 2013; 126:200-9, 10 pgs.

Uderzo C, et al., "Impact of thrombotic thrombocytopenic purpura on leukemic children undergoing bone marrow transplantation," Bone Marrow Transplant, 2000; 26:1005-9, 5 pgs.

Uderzo C, et al., "Risk factors and severe outcome in thrombotic microangiopathy after allogeneic hematopoietic stem cell transplantation," Transplantation, 2006; 82:638-44, 7 pgs.

Ueda N, et al., "Predictive Value of Circulating Angiopoietin-2 for Endothelial Damage-Related Complications in Allogeneic Hematopoietic Stem Cell Transplantation," Biology of Blood and Marrow Transplantation, 2014; 20:1335-40, 6 pgs.

Van Der Plas RM, et al., "von Willebrand factor proteolysis is deficient in classic, but not in bone marrow transplantation-associated, thrombotic thrombocytopenic purpura," Blood, 1999; 93:3798-802, 6 pgs.

Waters AM, et al. "aHUS caused by complement dysregulation: new therapies on the horizon," Pediatr Nephrol, 2011; 26:41-57, 17 pgs.

Willems E, et al., "Comparison of thrombotic microangiopathy after allogeneic hematopoietic cell transplantation with high-dose or nonmyeloablative conditioning," Bone Marrow Transplant, 2010; 45:689-93, 5 pgs.

Worel N, et al., "ABO-incompatible allogeneic hematopoietic stem cell transplantation following reduced-intensity conditioning: close association with transplant-associated microangiopathy," Transfus Apher Sci, 2007; 36:297-304, 8 pgs.

Wuhl E, et al., "Strict blood-pressure control and progression of renal failure in children," N Engl J Med, 2009; 361:1639-50, 12 pgs.

Yamada-Fujiwara M, et al., "Diagnosis of intestinal graft-versus-host disease and thrombotic microangiopathy after allogeneic stem cell transplantation," The Tohoku Journal of Experimental Medicine, 2012; 227:31-7, 8 pgs.

(56) References Cited

OTHER PUBLICATIONS

International Search Report and Written Opinion dated Dec. 31, 2014 for Application No. PCT/US2014/055922, 12 pgs.
Gralwohl, A., et al., "Current trends in hematopoietic stem cell transplantation in Europe," Blood, Oct. 2002, 100(7):2374-2386, 14 pgs.
Health Resources and Services Administration, US Department of Health and Human Services, "Transplant Activity Report," Apr. 15, 2017, 3 pgs.
Passweg, J.R., et al., "Hematopoietic stem cell transplantation in Europe 2014: more than 40,000 transplants annually," Bone Marrow Transplantation, 2016, 51:786-792, 7 pgs.
Japanese Office Action dated Nov. 30, 2018 for Application No. 2016-542879, 6 pgs.
Anderson, B.J., et al., "Tips and traps analyzing pediatric PK data," Pediatric Anesthesia, 2011, 21:222-37, 16 pgs.
Bauer, R.J., et al., "A Survey of Population Analysis Methods and Software for Complex Pharmacokinetic and Pharmacodynamic Models with Examples," The AAPS Journal, 2007, 9(1, Article7):E60-E83, 24 pgs.
Cho, B-S., et al., "Validation of Recently Proposed Consensus Criteria for Thrombotic Microangiopathy After Allogeneic Hematopoietic Stem-Cell Transplantation," Transplantation, 2010, 90:918-26, 9 pgs.
Dietrich, S., et al., "Endothelial Vulnerability and Endothelial Damage are Associated with Risk of Graft-versus-Host Disease and Response to Steroid Treatment," Biol Blood Marrow Transplant, 2013, 19:22-7, 6 pgs.
Feng, S., et al., "Partial ADAMTS13 deficiency in atypical hemolytic uremic syndrome," Blood, 2013, 122:1487-93, 7 pgs.
Gatault, P., et al., "Therapeutic drug monitoring of eculizumab. Rationale for an individualized dosing schedule," mAbs, 2015, 7(6):1205-1211, 7 pgs.
Goodwin JE, et al., "Glucocorticoid-induced hypertension," Pediatr Nephrol, 2012; 27:1059-66, 8 pgs.
Ishikawa Y, et al., "Transplantation-associated thrombotic microangiopathy after steroid pulse therapy for polyserositis related to graft-versus-host disease," Clin Exp Nephrol, 2011; 15:179-183, 5 pgs.
Jodele, S., et al., "Diagnostic and risk criteria for HSCT-associated thrombotic microangiopathy: a study in children and young adults," Blood, 2014, 124:645-53, 9 pgs.
Jodele, S., et al., "The genetic fingerpiint of susceptibility for transplant-associated thrombotic microangiopathy," Blood, 2016, 127:989-996, 8 pgs.
Keating, G.M., "Eculizumab: A Review of Its Use in Atypical Haemolytic Uraemic Syndrome," Drugs, 2013, 73:2053-66, 14 pgs.
Kim, S.S., et al., "Hematopoietic stem cell transplant-associated thrombotic microangiopathy: review of pharmacologic treatment options," Transfusion, 2015, 55:452-8, 7 pgs.
Laskin, B.L., et al., "Renal Arteriolar C4d Deposition: A Novel Characteristic of Hematopoietic Stem Cell Transplantation-Associated Thrombotic Microangiopathy," Transplantation, Jul. 2013, 96(2):217-23, 15 pgs.
Legendre, C.M., et al., "Terminal Complement Inhibitor Eculizumab in Atypical Hemolytic-Uremic Syndrome," N Engl J Med, 2013, 368:2169-81, 13 pgs.
McKeage, K., "Eculizumab: A Review of Its Use in Paroxysmal Nocturnal Haemoglobinuria," Drugs, 2011, 71:2327-45, 19 pgs.
Meri, S., "Complement activation in diseases presenting with thrombotic microangiopathy," European Journal of Internal Medicine, 2013, 24:496-502, 7 pgs.
Nadasdy T., "Thrombotic microangiopathy in renal allografts: the diagnostic challenge," Current opinion in organ transplantation, 2014; 19(3):283-292, 10 pgs.
Nehus EJ, et al., "Performance of cystatin C-based equations in a pediatric cohort at high risk of kidney injury," Pediatr Nephrol, 2013; 28:453-461, 9 pgs.
Peffault De Latour, R., et al., "Assessing complement blockade in patients with paroxysmal nocturnal hemoglobinuria receiving eculizumab," Blood, 2015, 125:775-83, 9 pgs.
Pio, R., et al., "Complement inhibition: a promising concept for cancer treatment," Seminars in Immunology, Feb. 2013, 25(1):54-64, 27 pgs.
Prasad, K., et al., "Prevention of bacterial meningitis: An overview of Cochrane systematic reviews," Respiratory Medicine, 2007, 101:2037-43, 7 pgs.
Rachakonda, S.P., et al., "Single-Nucleotide Polymorphisms Within the Thrombomodulin Gene (THBD) Predict Mortality in Patients with Graft-Versus-Host Disease," J Clin Oncol, 2014, 32(30):3421-7, 9 pgs.
Ricklin, D., et al., "Complement in Immune and Inflammatory Disorders: Pathophysiological Mechanisms," J Immunol, 2013, 190:3831-8, 8 pgs.
Ricklin, D., et al., "TMA: beware of complements," Blood, 2013, 122:1997-9, 3 pgs.
Roth C, et al., "The posterior reversible encephalopathy syndrome: what's certain, what's new?" Practical Neurology, 2011; 11:136-144, 9 pgs.
Schmidtko, J., et al., "Treatment of Atypical Hemolytic Uremic Syndrome and Thrombotic Microangiopathies: A Focus on Eculizumab," Am J Kidney Dis, 2013, 61:289-99, 11 pgs.
Schroder H., "Defibrotide Protects Endothelial Cells, but not L929 Tumour Cells, from Tumour Necrosis Factor-α-mediated Cytotoxicity," The Journal of Pharmacy and Pharmacology, 1995; 47:250-2, 3 pgs.
Shah, N., et al., "Role of ADAMTS13 in the management of thrombotic microangiopathies including thrombotic thrombocytopenic purpura (TTP)," Br J Haematol, 2013, 163:514-9, 6 pgs.
Staykov D, et al., "Posterior Reversible Encephalopathy Syndrome," Journal of Intensive Care Medicine, 2012; 27:11-24, 14 pgs.
Van Den Born, B-J., et al., "Association Between Thrombotic Microangiopathy and Reduced ADAMTS13 Activity in Malignant Hypertension," Hypertension, 2008, 51:862-6, 15 pgs.
Youden, W.J., Ph.D. "Index for Rating Diagnostic Tests," Cancer, 1950, 3:32-5, 4 pgs.
Zheng, S., et al., "Model-Based Assessment of Dosing Strategies in Children for Monoclonal Antibodies Exhibiting Target-Mediated Drug Disposition," CPT: Pharmacometrics & Systems Pharmacology, 2014, 3:e138, 10 pgs.
Canadian Office Action dated Nov. 30, 2018 for Application No. CA 2,921,856, 5 pgs.
European Exam Report dated Jan. 25, 2018 for Application No. 14843902.9, 4 pgs.
European Search Report, Supplementary, and Written Opinion dated Dec. 17, 2018 for Application No. EP 1680827.3, 8 pgs.
International Search Report and Written Opinion dated Feb. 7, 2019 for Application No. PCT/US2018/062210, 12 pgs.
Japanese Office Action, Notice of Reasons for Rejection, dated Nov. 30, 2018 for Application No. JP 2016-542879, 9 pgs. English Translation.
CH50 Eq, Enzyme Immunoassay Kit; For in-vitro diagnostic use only; Product code: MK095, The Binding Site Group, Ltd., Birmingham, UK, Sep. 21, 2009, pp. 1-3, 6 pgs.
"Importance of measuring blood concentration of drugs: Basic knowledge of TDM (monitoring)," Hiroshima Medical Association, Hiroshima, Japan, May 15, 2011, No. 542, pp. 2-5, 13 pgs.
Japanese Office Action, Notice of Reasons for Refusal, dated Sep. 26, 2019 for Application No. JP 2016-542879, 8 pgs.

* cited by examiner

FIG 10.

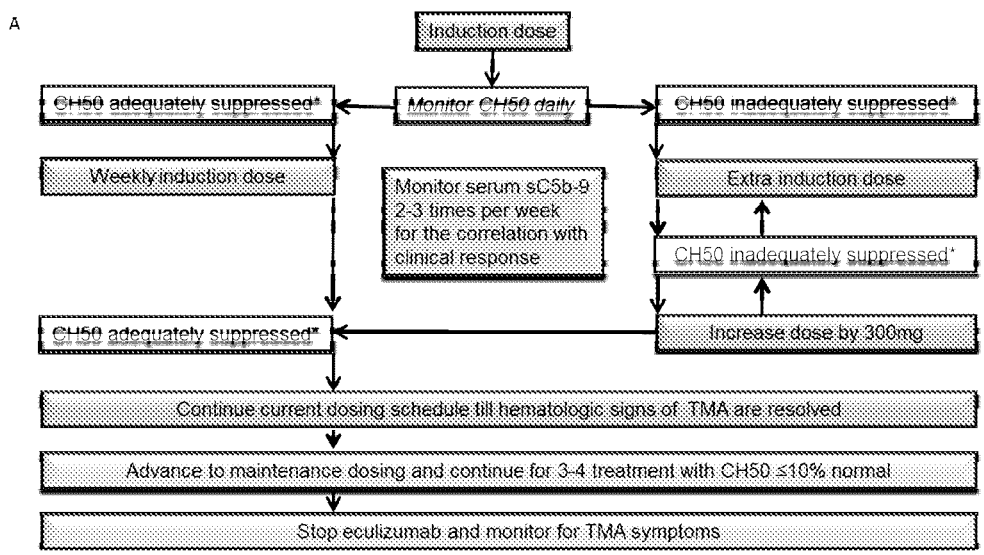

| Patient weight | Induction dose | Maintenance dose |
|---|---|---|
| 40 kg and over | 900 mg | 1200 mg every 2 weeks |
| 30 kg to less than 40 kg | 600 mg | 900 mg every 2 weeks |
| 20 kg to less than 30 kg | 600 mg | 600 mg every 2 weeks |
| 10 kg to less than 20 kg | 600 mg | 300 mg every 2 weeks |
| 5 kg to less than 10 kg | 300 mg | 300 mg every 2 weeks |

*adequate suppression of CH50 is 0-3 by enzyme immunoassay testing or 0-15 by hemolysis assay.

NOTE: If patient is receiving therapeutic plasma exchange (TPE), this procedure must be discontinued before starting eculizumab therapy in order not to remove medication from blood.

METHODS OF TREATMENT OF HSCT-ASSOCIATED THROMBOTIC MICROANGIOPATHY WITH ECULIZUMAB

PRIORITY

This application claims priority to and benefit of International Application Number PCT/US2014/055922, "Compositions and Methods for Treatment of HSCT-Associated Thrombotic Microangiopathy," filed Sep. 16, 2014 which claims priority to and benefit of U.S. Provisional Application 61/878,119, filed on Sep. 16, 2013, which are incorporated by reference in their entirety for all purposes.

BACKGROUND

In the United States, there are over 17,000 patients undergoing a hematopoietic stem cell transplant (HSCT or bone marrow transplant) each year for the treatment of malignancy, immunodeficiency, bone marrow failure, or genetic/metabolic syndromes. While survival has improved for these patients over the last decade, mortality after HSCT remains unacceptably high as almost 50% of patients are not alive seven years after transplant. Complications of HSCT are an important cause of morbidity in this patient population. One such complication, HSCT-associated thrombotic microangiopathy (HSCT-TMA, also referred to as TA-TMA), is also a significant cause of death after transplant. In those who survive the disease, HSCT-TMA may be associated with long-term morbidity affecting multiple organs with manifestations including hypertension, chronic kidney disease (CKD), gastrointestinal or central nervous system injury, and pulmonary hypertension.

The largest retrospective reviews report that the incidence of HSCT-TMA is 10-35% in patients undergoing HSCT. HSCT-TMA is defined clinically as the presence of new onset microangiopathic hemolytic anemia in an HSCT recipient: anemia and thrombocytopenia not explained by another process, elevated lactate dehydrogenase (LDH), excessive transfusion requirements, and schistocytosis in the blood. Relying on objective, organ-specific, non-invasive clinical criteria is critical to the timely recognition of HSCT-TMA after HSCT. While a biopsy remains the "gold standard" for diagnosing thrombotic microangiopathy in any patient population, a tissue diagnosis can be challenging in HSCT recipients or non-HSCT recipients who have a high risk of bleeding from low platelet and red blood cell counts and hypertension. The limited feasibility of tissue diagnosis after HSCT has led to the development of noninvasive diagnostic criteria for HSCT-TMA that has been updated several times, most recently by Applicant's group and serve for the clinical diagnosis of HSCT-TMA.

Severe hematopoietic stem cell transplant-associated thrombotic microangiopathy (HSCT-TMA) is a challenging post-transplant complication associated with long-term morbidity and high mortality. HSCT-TMA shares features with other thrombotic microangiopathies where endothelial injury affects the kidney and other organs. Mild HSCT-TMA can be present in a high proportion of HSCT recipients and typically has a benign course requiring no therapy or only modification of calcineurin inhibitor dosing. However, a proportion of cases will develop severe HSCT-TMA with hypertension and renal injury that may progress to a more generalized vascular injury with serositis, pulmonary hypertension, and multi-system organ failure. Targeted therapy is urgently needed for these patients in whom mortality is often the highest. For more than 30 years there had been significant obstacles in the search for targeted therapies for HSCT-TMA due to the limited understanding of this disease pathogenesis and overall complex nature of patients undergoing HSCT. The limited understanding of the pathogenesis of HSCT-TMA has hindered development and application of effective therapies.

While Applicant has discovered, as disclosed herein, that certain treatments may be effective in one or more of the disclosed disease states, Applicant further identified the problem that currently available methods of determining serum levels of the disclosed drugs could not be carried out in a timely manner. Such limitations in detecting serum levels prevent timely adjustments in the dosing of the disclosed drugs and effective treatment of the patient, which is of particular importance in the critically ill patient. As such, novel methods of determining serum levels of the disclosed drugs in patients, prior to Applicant's invention, was an unmet need in the art.

The instant disclosure seeks to address one or more of the aforementioned needs in the art.

BRIEF SUMMARY

Disclosed are drugs capable of inhibiting the complement pathway for use for treating hematopoietic stem cell transplant (HSCT) associated thrombotic microangiopathy (HSCT-TMA or TA-TMA) in a subject that has undergone an HSCT. Also disclosed are methods of using drugs capable of inhibiting the complement pathway for use for treating hematopoietic stem cell transplant (HSCT) associated thrombotic microangiopathy (HSCT-TMA or TA-TMA) in a subject that has undergone an HSCT.

BRIEF DESCRIPTION OF THE DRAWINGS

FIG. 8 depicts the diagnostic performance of CH50 level for predicting eculizumab concentration using the other available assay, a hemolytic method using standardized sheep erythrocytes (n=12). The optimal CH50 cutoff level for a therapeutic eculizumab trough level ≤99 µg/mL was determined based on an ROC curve (a) to maximize the Youden's Index which is defined as specificity+sensitivity−1(b). According to the analysis, the optimal CH50 cutoff level was found to be 15.5 CH50 units using this hemolytic assay (b). All the values were classified into two groups above and below the CH50 cutoff as shown in the panel c. The Y axis shows eculizumab concentrations in log-scale. The X axis shows the CH50 level by group. Horizontal lines represent medians. Posterior statistical analysis was performed to evaluate the difference in eculizumab concentration between the two groups by the Mann-Whitney's U test.

FIG. 10 depicts an eculizumab dose optimization schema.

DETAILED DESCRIPTION

Figure 1:
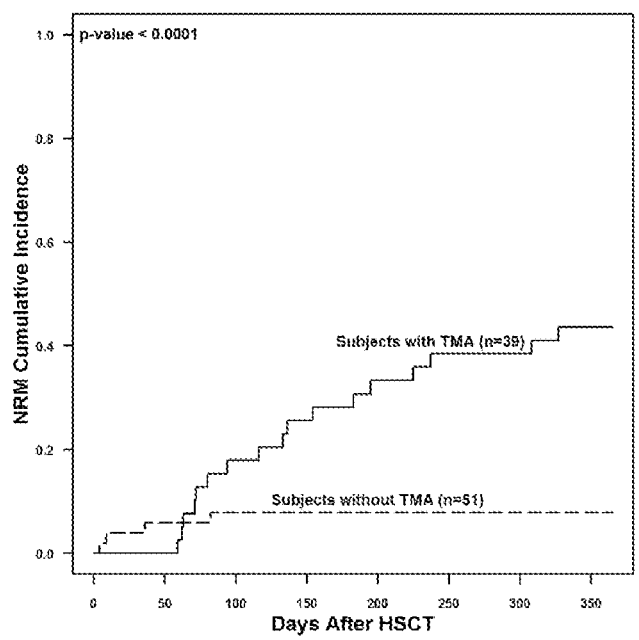
FIG. 1 depicts non-relapse mortality in patients with HSCT-TMA and without at 1 year after-HSCT. Gray's competing risk method was used to obtain the cumulative incidence of non-relapse mortality (NRM). The 1-year NRM for subjects with TMA was 43.6 (SE+−8%) and 7.8±3.8% in HSCT subjects without TMA (p<0.0001).

Unless otherwise noted, terms are to be understood according to conventional usage by those of ordinary skill in the relevant art.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "treating" means the administration of a composition to a subject, who has a disorder as described herein, with the purpose to cure, alleviate, relieve, remedy, prevent, or ameliorate the disorder, the symptom of the disorder, the disease state secondary to the disorder, or the predisposition toward the disorder.

As used herein, the term "therapeutically effective amount" or "effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. In general, such individual, host, subject or patient is a human, though other mammals are within the scope of the invention.

Other features, objects, and advantages of the present invention will be apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

Recently, Applicant documented complement system abnormalities in children with HSCT-TMA. Eculizumab, a humanized monoclonal antibody against the complement component C5, which serves to block the terminal complement pathway, is increasingly being prescribed in the treatment of diseases presenting with thrombotic microangiopathy, but its efficacy and dosing requirements in patients with HSCT-TMA were not known at the time of Applicant's invention as it had never been used before in this patient population. Applicant was the first to describe the efficacy of eculizumab in children with HSCT-TMA, and to report the importance of pharmacokinetic and pharmacodynamic monitoring to achieve effective complement blockade, as measured by total hemolytic complement activity (CH50).

The complement inhibitor eculizumab is increasingly prescribed in the treatment of diseases presenting with thrombotic microangiopathy, but has not been evaluated in hematopoietic stem cell transplant-associated thrombotic microangiopathy (HSCT-TMA). Eculizumab efficacy and dosing requirements in children with HSCT-TMA were not known prior to Applicant's invention.

For many years HSCT-TMA has been considered a separate and distinct disorder or entity occurring post-HSCT but without clearly defined disease causing pathogenesis. HSCT-TMA after HSCT shares some clinical and pathological features like thrombocytopenia, increased lactate dehydrogenase (LDH), microangiopathic changes, and kidney injury with other thrombotic microangiopathies that affect the non-bone marrow transplant population such as atypical hemolytic uremic syndrome (aHUS), thrombotic thrombocytopenic purpura (TTP), and pre-eclampsia/HELLP syndrome. Despite clinical and pathologic similarities for these TMAs, triggering factors and pathogenesis and targeted therapy can be different. For example, TTP is secondary to severely reduced activity of von Willebrand factor cleaving protease (ADAMTS-13). Pre-eclampsia/HELLP syndrome presents during pregnancy and results in vascular endothelial injury due to complement activation and usually resolved after childbirth. In aHUS, which is a very rare disease, >70% of patients have complement gene defects resulting in the alternative complement pathway activation and kidney injury and benefit from terminal complement blockade.

Prior to Applicant's invention, there was no evidence of a specific pathogenesis pathway for HSCT-TMA after HSCT. Without intending to be limited by theory, Applicant hypothesized that complement system was activated after HSCT and resulted in multi-organ vascular injury. Due to high inflammatory state in HSCT patients receiving chemotherapy or having graft versus host disease (GVHD) and/or infections, Applicant hypothesized that complement activation might occur and serve as a potential diagnostic and therapeutic target. Applicant examined TTP markers in patients with HSCT-TMA to support prior observation that HSCT-TMA is not simply TTP accruing after HSCT. Serum ADAMTS-13 activity can be moderately decreased in the setting of HSCT-TMA, especially in cases presenting with acute severe hemolysis, however is not severely decreased (<5-10% activity) as seen in patients with TTP and clearly rules out TTP diagnosis.

HSCT-TMA often presents as a multi-visceral disorder around 30 days after transplantation when patients are engrafting with donor stem cells. The multifactorial nature of endothelial injury that begins the HSCT-TMA process after HSCT makes it a distinct disease. Many of these factors, particularly GVHD and infections, may stimulate multiple complement pathways resulting in systemic vascular endothelial injury. Recipient and donor, or both, genotypes may play a significant role in tissue susceptibility to develop HSCT-TMA. Immune dysregulation occurring in the post-HSCT period may result in antibody formation against complement factors.

Risk Factors for HSCT-TMA

HSCT-TMA is more common after allogeneic HSCT, but also remains a significant complication of autologous transplantation. Risk factors associated in retrospective studies with the development of HSCT-TMA after allogeneic HSCT include medications used in the course of transplant and infectious complications. Conditioning agents including busulfan, fludarabine, cisplatin, and radiation may increase the risk of later HSCT-TMA. Other medications commonly reported to be associated with HSCT-TMA include the calcineurin inhibitors tacrolimus and cyclosporine and the newer mammalian target of rapamycin (mTOR) inhibitors. Viral infections are often considered to be a "trigger" for HSCT-TMA, as patients showing signs of small vessel injury can also have concomitant infections such as CMV, adenovirus, parvovirus B19, HHV-6, and BK virus.

Figure 2:
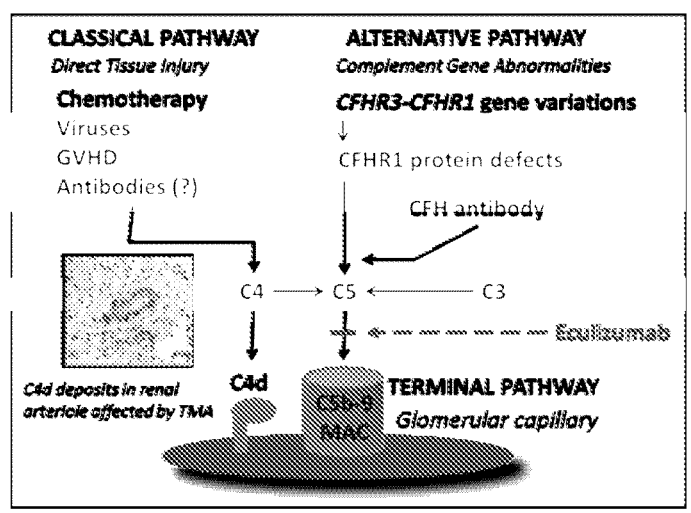
FIG. 2 depicts complement activation in HSCT-TMA.

Without intending to be limited by theory, Applicant hypothesized that dysregulation of the complement system was associated with organ injury in patients with HSCT-TMA and that blocking activated terminal complement (initially tested with the only clinically available medication, eculizumab) can be a potential treatment option for HSCT-TMA. Prior to Applicant's invention, there was no evidence in the literature that complement was involved in the pathogenesis of HSCT-TMA. Applicant hypothesized that either the classical or alternative complement system may be involved in HSCT-TMA, resulting in terminal complement activation and tissue injury, especially in the patients at highest risk for the worse outcomes, and that complement could be activated in HSCT patients as a result of direct tissue injury from cytotoxic therapy, immune dysregulation or triggered by infectious agents in patients with and without genetic predisposition. Also, due to very high likelihood of immune dysregulation after HSCT and interaction of donor and host phenotypes/genotypes, there was a possibility of anti-complement antibody formation as another complement mediated pathway of tissue injury in HSCT-TMA. Applicant hypothesized that complement modulating therapy with the only clinically available terminal complement blocker eculizumab could serve as targeted treatment for HSCT-TMA (FIG. 2). Likewise, Applicant theorizes that other terminal complement blockers could similarly achieve this effect.

Figure 5:
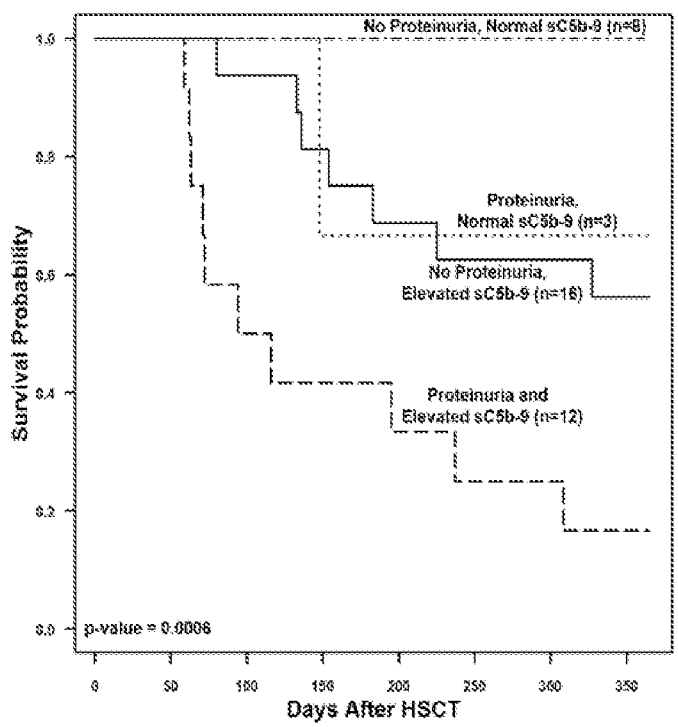
FIG. 5 depicts Kaplan-Meier survival curves for subjects with TMA (n=39) without proteinuria and normal sCSb-9, proteinuria ≥30 mg/dL and normal sCSb-9, no proteinuria and elevated sCSb-9, and both proteinuria ≥30 mg/dL and elevated sCSb-9 at the time of HSCT-TMA diagnosis.

With the challenges in using clinical diagnostic criteria available at the time of this invention, Applicant further investigated complement involvement and complement marker use for disease risk stratification to be able to optimize complement blocking therapy in HSCT-TMA. (FIG. 5). Finally, in the absence of readily available eculizumab serum measurement, Applicant identified a surrogate marker that would correlate with the eculizumab level in patient's serum and that would provide a much faster turnaround time than available methods that could be used for real-time drug dosing adjustment in clinical care.

Compositions

In one aspect, a drug capable of inhibiting the complement pathway for use for treating hematopoietic stem cell transplant (HSCT) associated thrombotic microangiopathy (HSCT-TMA) in a subject that has undergone an HSCT is disclosed.

In certain aspect, the drug may comprise a drug or an antibody capable of inhibiting the complement pathway. In one aspect, the antibody may comprise a monoclonal antibody capable of inhibiting the complement pathway. In other aspects, the drug may comprise a humanized monoclonal antibody capable of inhibiting the complement pathway. In certain aspects, the drug may be eculizumab, available from Alexion Pharmaceuticals®, and sold under the trade name Soliris®.

In one aspect, the use of the drug may be repeated every day, or every two days, or every three days. The drug may be used in at least one dose, or at least two doses, or at least three doses, or at least four doses, or in certain aspects, more than four doses. In one aspect, the use may be carried out until a hematological response or a complete disease response is achieved in the subject. In certain aspects, the use may be carried out over a period of about four to about 15 weeks, or longer. In certain aspects, the drug is administered weekly. The drug may be is administered via any method as is known in the art, for example, intravenously, subcutaneously, intramuscularly, and/or orally.

Methods

Also disclosed is a method for monitoring the efficacy of a treatment with a complement inhibitor against HSCT associated thrombotic microangiopathy (HSCT-TMA) in a subject that has undergone an HSCT, which may comprise the step of measuring of total complement activity (CH50) in a serum sample of the subject. In certain aspects, the subject may be administered a complement inhibitor until the CH50 measurement in the serum from the subject is from about 0-3 CAE units as measured by enzyme immunoassay, or until the CH50 measurement in the subject is less than 15 CH50 units as measured by a hemolytic method.

The method may further comprise the step of measuring total complement activity (CH50) in a subject prior to treatment of the subject with a complement inhibitor to obtain an initial CH50 measurement.

Also disclosed is a method of treating HSCT associated thrombotic microangiopathy (HSCT-TMA) in a subject that has undergone a bone marrow transplant. The method may comprise the step of administering a drug or an antibody capable of inhibiting terminal complement. The terminal complement may comprise a monoclonal antibody capable of inhibiting terminal complement, or in another embodiment, a humanized monoclonal antibody capable of inhibiting terminal complement, or in yet another embodiment, the antibody may be eculizumab.

The administration step may be carried out in a manner sufficient to achieve a therapeutic level in the subject. In certain aspects, the therapeutic level may comprise a blood serum level of greater than or at least about 99 μg/mL, or at least or greater than about 100 μg/mL, or at least or greater than about 200 μg/ml, or at least or greater than about 300 μg/ml.

The administration step may be repeated daily, or every two days, or every three days until a serum level of greater than or at least about 99 μg/mL, or at least or greater than about 100 μg/mL, or at least or greater than about 200 μg/ml, or at least or greater than about 300 μg/ml is achieved in the subject. Determination of the dosage in a patient based on patient weight will be readily understood by one of ordinary skill in the art.

The administration step may be carried out in a manner sufficient to achieve a therapeutic eculizumab level in the subject. The administration step may comprise at least one dose, or at least two doses, or at least three doses, or at least four doses, or, in some aspects, more than four doses. The method, may further comprise the step of measuring total complement activity (CH50) to obtain a CH50 measurement, wherein the subject is administered the complement inhibitor until the CH50 measurement obtained from the patient is from about 0-3 CAE units as measured by enzyme immunoassay, or wherein the CH50 measurement is 0-15 CH50 units as measured using a hemolytic method using standardized sheep erythrocytes. In one aspect, the method may further comprise the steps of a) measuring total complement activity (CH50) prior to treatment with a complement inhibitor to obtain an initial CH50 measurement; b) administering a complement inhibitor; and c) measuring total CH50 activity after administration of the complement inhibitor to obtain a post-treatment CH50 measurement, wherein said complement inhibitor is administered until said post-treatment CH50 measurement is from about 0-3 CAE units as measured by enzyme immunoassay, or wherein the CH50 measurement is 0-15 CH50 units as measured using a hemolytic method using standardized sheep erythrocytes.

The administration step may comprise administering eculizumab, and the administration step may be carried out for a period of time sufficient to resolve HSCT-TMA. In some aspects, the administration step is carried out over a period of about four to about 15 weeks, or up to 20 weeks, or up to 25 weeks, or until eculizumab is at a dosage sufficient to reduce CH50 levels to 0-3 CAE units as measured by enzyme immunoassay, or wherein the CH50 measurement is 0-15 CH50 units as measured using a hemolytic method using standardized sheep erythrocytes.

The administration step may comprise administering eculizumab, and the administration step may be carried out for a period of time sufficient to achieve a favorable hematologic response, wherein a favorable hematological response comprises resolution of hematologic HSCT-TMA markers. The markers may include, but are not limited to, normalization of LDH, resolution of need for red cell and platelet transfusions, and disappearance of schistocytes, or any other such criteria as will be readily understood by one of ordinary skill in the art.

The administration step may be carried out over a period of time sufficient to achieve a complete response, wherein the complete response comprises normalization of said subject's hematologic parameters and renal response, including, but not limited to, a doubling of the cystatin C-estimated glomerular filtration rate (eGFR) and improvement of proteinuria to values below the nephrotic range as defined by random spot urine protein to creatinine ratio below 2 mg/mg, or other criteria as will be readily understood by one of ordinary skill in the art.

In certain aspects, the subject may be administered eculizumab multiple times a day, daily, weekly, or monthly. If the initial or subsequent dose is not therapeutic, an additional dose may be administered on a daily, weekly, or monthly basis. In such cases, the additional dose may be a larger dose than the initial or most recent dose administered. In certain aspects, the dose may be increased by about 100 mg, or about 200 mg, or about 300 mg, or about 400 mg, or about 500 mg.

In one aspect, a method of determining the relative levels of a complement inhibitor in a subject administered a complement inhibitor is disclosed. In this aspect, the method may comprise the step of measuring total complement activity (CH50) in a sample obtained from the subject. The total complement inhibitor may comprise, for example, eculizumab.

In one aspect, a method of optimizing an eculizumab dosing schedule in a subject having any syndrome of TMA, post-HSCT or not, is disclosed. In this aspect, the method may comprise the step of determining total complement activity (CH50) in said subject who is treated by an induction dose of eculizumab; wherein if CH50 levels are not adequately suppressed (as used herein, "adequately suppressed" means 0-3 CAE units as measured by enzyme immunoassay, or 0-15 CH50 units as measured using a hemolytic method using standardized sheep erythrocytes, as described herein), a second induction dose is administered; wherein if CH50 levels are adequately suppressed, said patient is administered a weekly induction dose; wherein if CH50 levels are inadequately suppressed after said second induction dose, said induction dose is increased by from about 100 mg to about 400 mg, preferably about 300 mg; wherein said subject is administered eculizumab until hematologic signs of TMA are resolved. The method may further comprise the step of providing a maintenance dose to maintain CH50 suppression. The induction dose may be selected from about 900 mg eculizumab for subjects weighing 40 kg or greater, about 600 mg eculizumab for subjects weighing about 30 kg to about 40 kg, about 600 mg eculizumab for subjects weighing about 20 kg to about 30 kg, about 600 mg eculizumab for subjects weighing about 10 kg to about 20 kg, about 300 mg eculizumab for subjects weighing about 5 kg to about 10 kg.

Examples

Classical Complement Pathway

Complement Deposits are Found in Kidney Arterioles in Patients with HSCT-Associated TMA In order to address our concept of complement mediated vascular injury after HSCT, Applicant examined kidney tissue specimens from patients after HSCT who developed HSCT-TMA and those who did not. Applicant determined that patients with histologic evidence of HSCT-TMA have significant C4d deposits in renal arterioles representing classical complement mediated vascular injury.

Figure 3:
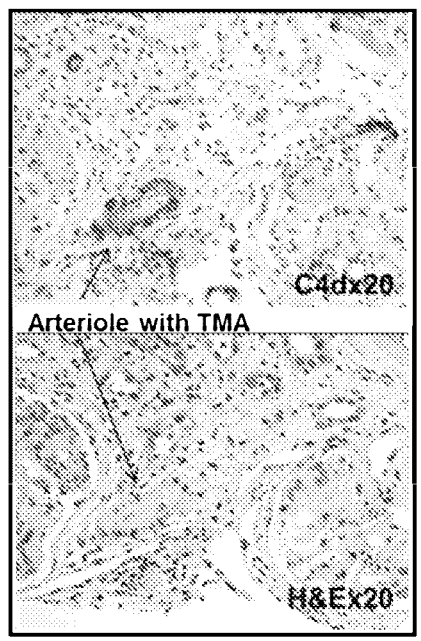
FIG. 3 depicts C4d deposits in kidney arterioles affected by TMA. Representative renal biopsy specimen from a subject with histologic evidence of HSCT-TMA after hematopoietic stem cell transplantation. A, hematoxylin and eosin staining (H&E magnification, ×20) of renal cortex with glomeruli. Small arterioles (arrows) show obliteration of the vessel lumen due to sloughed endothelial cells, intimal proliferation, and extracellular matrix deposition indicative of TMA. C4d staining (C4d magnification, ×20) of corresponding tissue section shows diffuse positive staining in the degenerating small arteriole with microangiopathic changes. C4d stains were performed in the clinical pathology laboratory at CCHMC using techniques certified for clinical test use (CLIA approved lab). Arteriolar C4d deposits were almost exclusively found in patients with HSCT-TMA as compared to HSCT patients without HSCT-TMA (% (75%) vs 1/12 (8%) p=0.004). This was the first evidence of complement deposits in the arterioles from subjects with TMA after HSCT, supporting classical complement involvement in vascular injury with HSCT-TMA and possibly explaining the severe hypertension observed in patients with HSCT-TMA.

In brief, kidney tissue specimens from 20 HSCT patients were examined for complement deposits using C4d staining (FIG. 3). Specimens were divided into a TMA group (n=8) if they had histologic evidence of TMA and an HSCT control group (n=12) without histologic evidence of TMA. C4d staining was performed at the clinical pathology laboratory at CCHMC and was graded by two clinical pathologists, blinded to each subject's original pathological diagnosis. C4d staining was evaluated in all histologic kidney compartments and was graded as diffuse (>50%), focal (10-50%) and rare (1-10%) or negative (0%). Diffuse arteriolar C4d staining was predominant in patients with TMA as compared to controls (p=0.004). Rare peritubular capillaries (PTC) C4d staining was present in half of the subjects with TMA and was absent in controls. Glomerular C4d staining was common and nonspecific in both groups (p=0.35). Rare focal tubular basement membrane staining was found in a third of subjects with TMA and was absent in controls.

TABLE 1

C4d staining in different kidney compartments in patients with HSCT-associated TMA

| Group | Arterioles* | PTC | Glomerulus | Basement membrane |
|---|---|---|---|---|
| TMA | 6/8 (75%) | 4/8 (50%) | 5/8 (63%) | 3/8 (38%) |
| HSCT control | 1/12 (8%) | 0/12 (0%) | 10/12 (83%) | 0/12 (0%) |

*p = 0.004

The only prior observations examining C4d deposits in the kidney after HSCT was reported by Mii et al concluding that positive Cd4 staining in renal glomeruli after HSCT is likely representation of graft versus host disease (GVHD), but this study did not have any control group.

Arteriolar staining with C4d has not been reported in other disorders outside Applicant's observation in HSCT-TMA. On the other hand, peri-tubular capillary (PTC) staining for C4d is strongly correlated with worse kidney allograft survival and likely reflects the presence of complement fixing donor-specific anti-HLA antibodies. C4d has been also correlated with tissue injury and worse clinical outcomes in recipients of other solid organ transplants, including heart, pancreas, and liver allografts, whereas glomerular staining is commonly reported in known complement mediated diseases and other conditions with immune complex deposition, such as lupus nephritis.

Terminal Complement Pathway

To address possible terminal complement involvement in pathogenesis of HSCT-TMA that would support the concept of use of terminal complement blocker eculizumab in HSCT-TMA Applicant examined terminal complement activation by measuring sC5b-9 in serum of HSCT patients with and without HSCT-TMA. sC5b-9 testing was performed at CCHMC hematology laboratory using methodology approved for clinical patient testing (CLIA certified lab).

Figure 4:
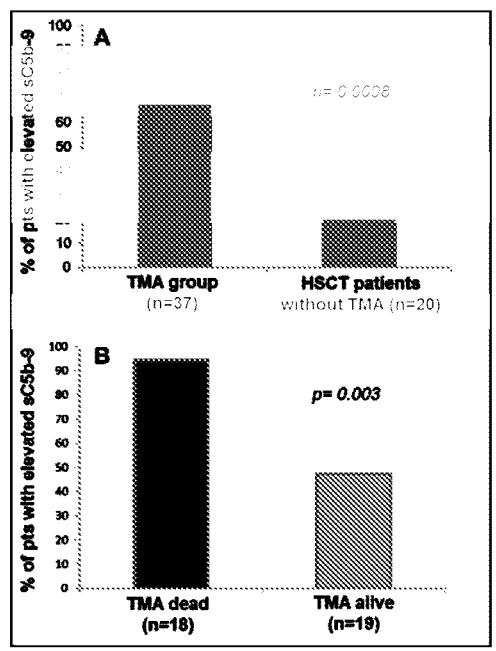
FIG. 4 depicts terminal complement activation in HSCT patients with HSCT-TMA and without HSCT-TMA.

To measure terminal complement activation in HSCT patients with TMA and HSCT patients without TMA enzyme immunoassay (EIA) for the Soluble Terminal Complement Complex SC5b-9 in plasma (normal<244 ng/mL) was used. sC5b-9 is generated by the assembly of C5 through C9 as a consequence of activation of the complement system by either the classical, lectin or alternative pathway. The membrane attack complex (MAC), a form of sC5b-9, is a stable complex that mediates the irreversible target cell membrane damage associated with complement activation. Complexes formed in the absence of a target membrane bind to naturally occurring regulatory serum proteins, e.g. the S protein forming non-cytolytic complexes in plasma. sC5b-9 was measured in 37 patients with HSCT-TMA at HSCT-TMA diagnosis and 20 HSCT without TMA at day 30 (+/−3 days) after HSCT (risk time to develop HSCT-TMA) and showed significantly more patients with HSCT-TMA having elevated sC5b-9 (67% vs 20%, p=0.008) (FIG. 4, A). Also compared was sC5b-9 in TMA patients who died by one 1 year post-transplant with active HSCT-TMA vs in those HSCT-TMA patients who survived and showed that significantly more patients who died with active HSCT-TMA had elevated sC5b-9 (94% vs 47%, p=0.003) (FIG. 4, B) and levels were highest in those who died of HSCT-TMA (289 ng/mL (range 100-415) vs 445 ng/mL (range 174-971). This data shows that terminal complement activation contributes to development of HSCT-TMA and is associated with poor overall outcome after HSCT.

Complement Activation is a High Risk Feature in HSCT-TMA

We carried out a prospective study on 100 pediatric and young adult patients to examine risk features of HSCT-TMA in regards to complement system activation. Thirty nine subjects (39%) met published criteria for HSCT-TMA. Subjects with HSCT-TMA had a significantly higher non-relapse mortality (43.6% versus 7.8%, p<0.0001) at 1 year post-HSCT compared to those without HSCT-TMA (FIG. 1). Elevated lactate dehydrogenase (LDH), proteinuria on routine urinalysis, and hypertension were the earliest markers of HSCT-TMA (FIG. 5).

Proteinuria (>30 mg/dL) and evidence of terminal complement activation (elevated sC5b-9) in the blood at the time of HSCT-TMA diagnosis were associated with very poor survival (16% at 1-year), while all HSCT-TMA subjects without proteinuria and a normal sC5b-9 serum concentration survived (p<0.01). Based on these prospective observations, Applicant concluded that 18% of all transplanted patients presented with severe HSCT-TMA and complement system activation that affected their outcome.

HSCT-TMA Response to Eculizumab

Based on our concept that complement activation is responsible for systemic vascular injury in patients with HSCT-TMA Applicant treated pilot group of patients with eculizumab.

All patients treated had high risk HSCT-TMA features including elevated sC5b-9 serum level at HSCT-TMA diagnosis and multi-organ involvement. Since there was no data available on eculizumab use in the HSCT population, Applicant hypothesized that HSCT patient will likely require different medication dosing than currently used for the only currently approved indications of paroxysmal nocturnal hemoglobinuria (PNH) or aHUS. A diagnosis of TTP was ruled out prior to starting therapy.

Applicant defined a response to eculizumab using these criteria: A hematologic response to eculizumab was defined as normalization of lactate dehydrogenase (LDH), resolution of the need for red blood cell and platelet transfusions, and disappearance of schistocytes. A complete response was defined as normalization of the hematologic parameters noted above combined with a doubling of the cystatin C-eGFR and improvement of proteinuria to values below the nephrotic range, as defined by a random spot urine protein to creatinine ratio <2 mg/mg.

Therapeutic plasmapheresis was stopped in all patients receiving prior to starting eculizumab, so as not to wash out the medication. Applicant theorized that alternative markers might be indicative of eculizumab blood levels. Diagnostic functional complement system assessment included but was not limited to measurements of sC5b-9, CH50, and complement factor H autoantibody. While eculizumab serum level testing was available clinically at Cambridge Biomedical laboratory, results were only available in the medical record in 4-10 days and could not be used for timely drug level assessment for prompt clinical care. Such testing was used, however, for later correlation with other markers.

In the absence of any data in the HSCT population, we proposed to target eculizumab level at least 99 μg/mL (based on dosing in aHUS) or above for HSCT patients treated for HSCT-TMA. Data was available that higher eculizumab serum level does not pose additional side effects. Also, in the absence of readily available eculizumab serum measurements, we opted to identify a surrogate marker that would correlate with eculizumab level of >99 μg/mL in patient's serum and had much faster turnaround time useful for real-time drug dosing adjustment in clinical care. The first eculizumab dose was given based on patient weight using eculizumab drug information.

To examine our concept of different dosing requirements in HSCT-TMA after HSCT, we selected to monitor total complement hemolytic activity (CH50) and correlate it with eculizumab serum levels and clinical response. For the first 6 patients initially treated, Applicant measured CH50 prior to starting eculizumab and daily thereafter during induction therapy clinically available using the enzyme immunoassay.

Total hemolytic complement activity (CH50) was measured in serum during eculizumab therapy as a pharmacodynamic marker of eculizumab induced complement blockade, at the same time points as eculizumab drug levels. There are two main methods used for measuring CH50: an enzyme immunoassay method and a hemolytic method using standardized sheep erythrocytes, to measure CH50 and Applicant examined both of them in patients treated with eculizumab.

The pharmacokinetic profiling of eculizumab was performed at the Division of Clinical Pharmacology, Cincinnati Children's Hospital Medical Center (CCHMC), and was described by a one-compartment model since the eculizumab concentrations showed an exponential decline over time. The elimination rate constant (kel) and concentration at 0 (C0) were estimated by linear least-squares regression of the log-transformed concentrations versus time in the log-linear phase of the disposition profile. Apparent volume of distribution (Vd) was estimated based on Dose/C0 in the first treatment. Apparent systemic clearance (CL) was calculated by the formula; $CL(L/h)=kel*Vd$. Maximum eculizumab concentrations in the $n^{th}$ dose ($C_{max,n}$) were determined by the following equation: $C_{max,n}=C_{trough,n-1}+Dose/Vd$. Receiver operating characteristics (ROC) curve analysis and Youden's index were used to find the best cut-off value of CH50 that predicted a therapeutic eculizumab trough level >99 μg/mL.

Figure 6:
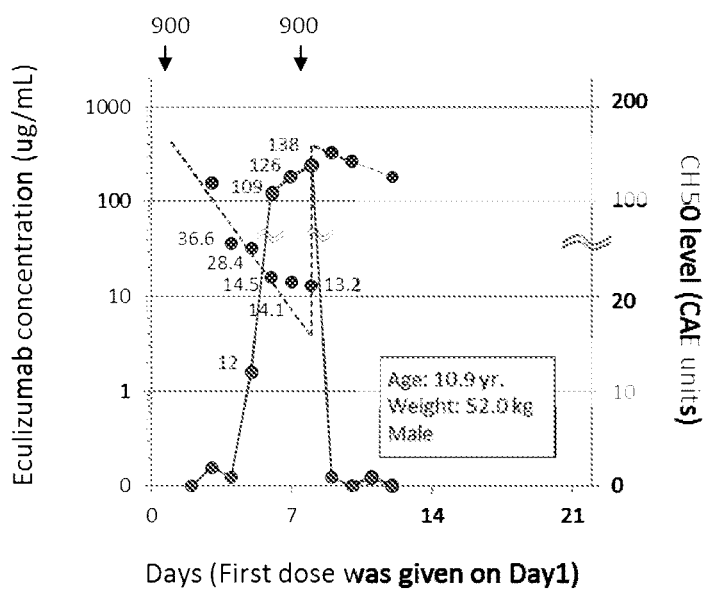
FIG. 6 depicts longitudinal correlation of CH50 and eculizumab serum levels. Depicted is a representative correlation of eculizumab daily serum level (dashed line) with CH50 level (solid line). The previously reported eculizumab level required to block terminal complement of 99 µg/mL was established in patients with a different disorder, atypical hemolytic uremic syndrome, aHUS. This graph clearly shows that as eculizumab levels drop below 99 µg/mL, the CH50 level quickly rises in subjects with HSCT-TMA after HSCT. This graph also illustrates that the eculizumab level is not sustained above >99 µg/mL for 1 week using currently approved dosing regimen for aHUS and therefore pharmacokinetic dose monitoring is required in HSCT patients with HSCT-TMA to determine the required dose (mg) and timing to sustain clinically significant inhibition of the complement pathway.

Eculizumab and CH50 levels that were measured at the same time points strongly correlated with each other—as the eculizumab serum level was declining, CH50 was rising (FIG. 6). Our next step in pharmacodynamic evaluation was to examine the diagnostic performance of CH50 level for predicting an eculizumab concentration of >99 μg/mL by using 2 standard methods: enzyme immunoassay method and using a hemolytic method using standardized sheep erythrocyte.

Figure 7:
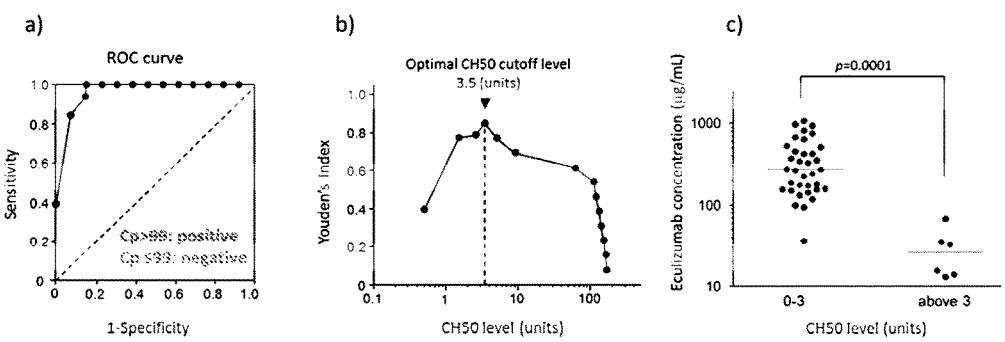
FIG. 7 depicts the diagnostic performance of the CH50 level for predicting the eculizumab concentration using enzyme immunoassay method (n=6). The optimal CH50 cutoff level associated with an eculizumab trough level >99 µg/mL was determined based on an ROC curve (a) to maximize the Youden's Index which is defined as specificity+sensitivity−1(b). According to the analysis, the optimal CH50 cutoff level was found to be 3.5 CAE units (b). All values were classified into two groups above and below this CH50 cutoff as shown in the panel c. The Y axis shows eculizumab concentrations in log-scale. The X axis shows the CH50 level by group. Horizontal lines represent medians. Posterior statistical analysis was performed to evaluate the difference in eculizumab concentration between the two groups by a Mann-Whitney's U test. A CH50 level of 0-3 CAE units corresponded with an eculizumab concentration of >99 µg/mL in all except for one measurement (drawn from a patient during an extremely rapid elimination phase in the first week of therapy). Conversely, at all sampling time points a CH50 level >3 CAE units corresponded with a sub-therapeutic level of ≤99 µg/mL (p=0.0001).

Enzyme Immunoassay Method (FIG. 7):

A CH50 level measured by enzyme immunoassay method of 0-3 CAE units corresponded with an eculizumab concentration of >99 μg/mL (FIG. 7). Conversely, at all sampling time points with a CH50 count of ≥4 CAE units, the patients' eculizumab concentrations were below 99 μg/mL (p=0.0001). CH50<3 CAE units correlated with serum eculizumab of at least 99 μg/mL or higher (Normal CH50 level by this method is 60-144 CAE).

The CH50 immunoassay used is that available from the Binding Site, www.thebindingsite.com, CH50 Assay (EIA Method), Product number MK095. The Complement Activation EIA (CAE) test kit is a novel method for measurement of total classical complement activity. This method uses an enzyme-conjugated monoclonal antibody specific for neoantigen of terminal complement proteins. Microtiter wells are coated with complement activator into which a single dilution of patient or control serum is added. The complete classical complement pathway is activated and the cascade of C1q through C9 is formed within the well of the microtiter plate. Horseradish peroxidase-conjugated monoclonal antibody is allowed to react with the resulting neoantigen bound to the plate wells. After addition of chromogen, quantitation is achieved by comparison of the resultant absorbances, measured at 450 nm, to a reference, and verified by two controls.

Hemolytic Method

Figure 8A:
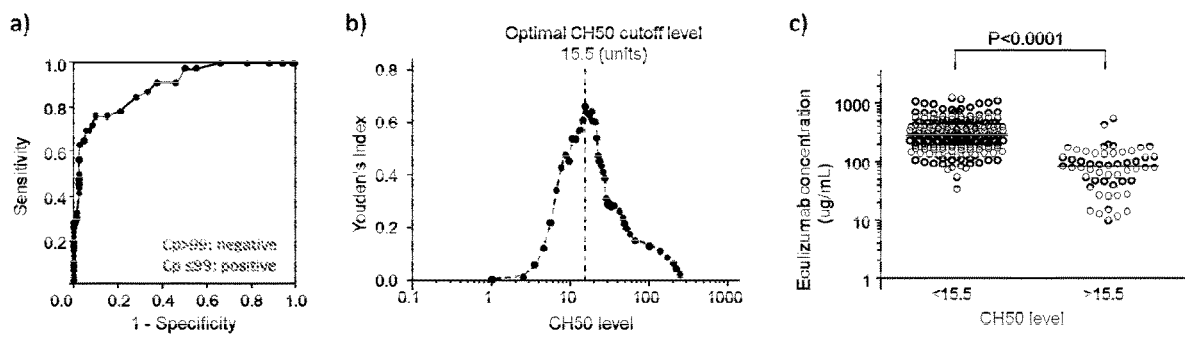
FIG. 8*a* is data obtained during therapy with eculizumab.
Figure 8B:
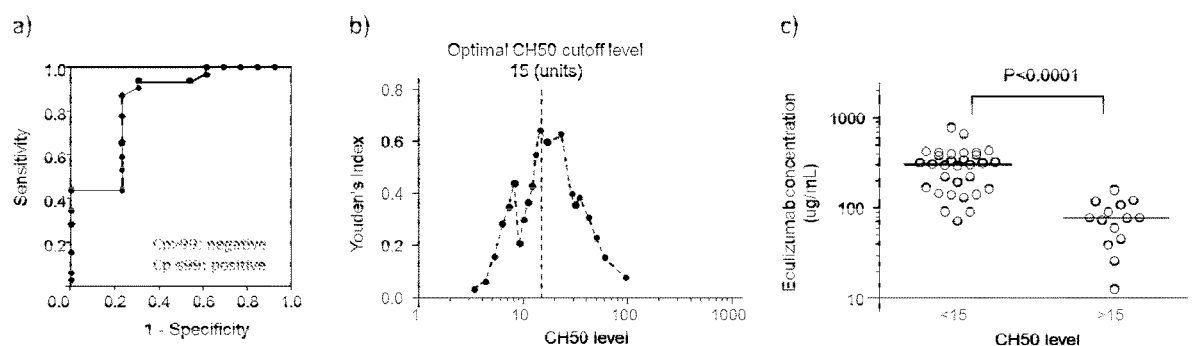
FIG. 8*b* depicts data obtained after the first and second eculizumab doses.

Later, Applicant treated another twelve patients with high risk HSCT-TMA; CH50 levels in these patients were determined using the hemolytic method using standardized sheep erythrocyte (FIG. 8). FIG. 8 displays correlation of CH50 with eculizumab concentration of >99 μg/mL by using a hemolytic method using standardized sheep erythrocytes (n=12). CH50 level 0-15 CH50 units corresponded with an eculizumab concentration of >99 μg/mL (FIG. 8) during all therapy (A) and during first and second dose analyzed separately (B). (Normal CH50 level by this method is 101-300 CH50 units).

The Hemolytic CH50 Method is as follows:

Principle

The traditional method for determination of functional complement activity is the total hemolytic (CH50) assay. This assay measures the ability of the test sample to lyse 50% of a standardized suspension of sheep erythrocytes coated with anti-erythrocyte antibody. Both the classic activation and the terminal complement components are measured in this reaction.

Method

The CH50 Complement test is a hemolytic assay using sensitized sheep erythrocytes, available from Diamedix Corporation. The cells are sensitized by antibody against the sheep erythrocytes, and an antigen-antibody complex is formed. When exposed to complement in human serum, lysis of the erythrocytes will occur and free hemoglobin is released. The degree of lysis is proportional to the concentration of total complement in the human serum. The resulting hemolysis is read at 415 nm and compared to a reference serum of known concentration.

Sample Requirements

Human serum is stored frozen at −20° C. for samples within 24 hours. Hemolyzed samples are not used. During testing, the sample is thawed and mixed, then remain cold at 2-8° C. until use.

Reagents

EZ Complement Cells (Diamedix Corporation, Catalog No. 789-001)

EZ Complement Reference Serum (EZ Complement Standard, Diamedix Corporation, Catalog No. 789-006)

EZ Complement Low Control and EZ Complement High Control (Diamedix Corporation, Catalog Nos. 789-008 & 789-009)

Storage Requirements

The EZ Complement Cells should be stored at 2 to 8° C. Controls and

Reference serum are stored at 0° C. to −20° C. The reagents are stable until the expiration date listed on the box.

Materials & Equipment

Pipettes

Tube rack

Vortex

Timer

Centrifuge

Microplate reader (415 nm)

Preparation of Reference and Quality Control

The Reference Serum and Quality Control materials are lyophilized human serum. They are reconstituted prior to use with 300 μl cold distilled water and mixed gently and allowed to remain at room temperature for five minutes. The vials remain on ice for an additional 10 minutes before using. Once reconstituted, they are tested within 8 hours.

Procedure

1. As many tubes as there are patients are prepared, as well as one each for Low and High QC, Blank (spontaneous lysis), and Reference (standard).

2. The tubes are allowed to remain at room temperature for at least 1 hour prior to beginning test.

3. Prepare QC and Reference serum as indicated above.

4. Vortex tubes for 10 seconds to re-suspend cells.

5. Remove caps from all tubes.

6. Add 5 μl of patient sample, controls, and reference serum to appropriately labeled tube, replace cap and shake vigorously to mix.

7. The Blank tube should also be mixed.

8. Allow tubes to stand at room temperature (18-30° C.) for 1 hour.

9. Mix tubes by inverting 3-4 times.

10. Centrifuge tubes for 10 minutes at 1800 rpm.

11. Pipette 200 μl of each sample in duplicate onto a 96 well plate.

12. Read at 415 nm.

Validation

The absorbance of the Blank (spontaneous lysis) must be less than 0.150. The quality control values must be within expected range.

Analysis

The absorbance of the Blank tube will be subtracted from the absorbances of the test samples to correct for the degree of spontaneous lysis that may occur in the test samples.

The results are calculated using the following formula to obtain CH50 units:

$$\text{Absorbance of Sample} \times \text{CH50 Value} = \text{CH50 Value of Sample}$$

Absorance of Reference

Quality Control

There are two levels of quality control provided with the kit.

Documentation of Quality Control Data:

A worksheet is used for each run to document the quality control, kit lot number and expiration date. The ranges of each control are available for review on the worksheet. The Cerner Laboratory Reporting System is used to report quality control and patient results for each assay performed.

Reference Range

Absent or Low 0-100

Normal 101-300

High >301

REPORTING FORMAT Results are reported in CH50 Units. The test is linear from zero to 400 CH50 units.

Measuring Range

Linearity studies showed that the assay is linear to 400 CH50 Units when compared to "gold standard" material.

In summary, adequately suppressed CH50 level for clinical use will be below 4 CAE on if measured by enzyme immunoassay method and below 15 CH50 units if measured by hemolytic method using standardized sheep erythrocytes. These levels will be referred as "adequately suppressed CH50 in eculizumab dosing optimization" schema.

Applicant initially published findings on six children who were treated for HSCT-TMA with eculizumab using dose modifications based on drug pharmacokinetics. Total hemolytic complement activity (CH50) was measured as a pharmacodynamic endpoint at the same time as eculizumab levels. Four of six children had resolution of HSCT-TMA once therapeutic eculizumab levels and complete complement blockade was achieved. Two patients failed to achieve therapeutic eculizumab levels, even after dose escalation, and subsequently died. Complement blockade, as measured by CH50, correlated with therapeutic eculizumab levels and clinical response.

The six consecutive patients with severe HSCT-TMA who were treated with eculizumab (Alexion, Conn., USA) at Cincinnati Children's Hospital Medical Center (CCHMC) between January 2012 and May 2013 were initially included in the analysis. The Institutional Review Board approved retrospective chart review. Patient demographics, therapy characteristics, and HSCT complications were abstracted from the medical record. HSCT-TMA was diagnosed using current diagnostic criteria and included elevated lactate dehydrogenase (LDH) above normal for age, haptoglobin below the lower limit of normal, schistocytes on peripheral blood smear, anemia, thrombocytopenia, a negative Coombs test, and acute kidney injury, defined as a doubling of the serum creatinine or a 50% decline in estimated cystatin C glomerular filtration rate (eGFR, normal 80-120 mL/min) from each subject's pre-HSCT baseline. Proteinuria was identified using a random spot urine protein to creatinine ratio (normal<0.2 mg/mg, nephrotic range >2 mg/mg). Kidney biopsy results, if available, were reviewed for histology of TMA. Each subject's legal guardian signed informed consent for treatment with eculizumab.

Eculizumab Treatment and Monitoring

Therapeutic plasma exchange (TPE) was stopped in patients receiving it prior to starting eculizumab so as not to remove the drug, as TPE washes out the medication. The first dose of eculizumab was given according to recommendations for children with atypical hemolytic uremic syndrome (aHUS) (Table 2). Eculizumab was infused via central venous access over 30-60 minutes. Because immune compromised HSCT recipients do not respond to meningococcal vaccination, all patients were maintained on ciprofloxacin or penicillin VK prophylaxis until eculizumab was cleared and the CH50 levels normalized. Eculizumab levels in serum were tested at least twice a week after each dose, including a trough level drawn prior to each dose. Eculizumab drug levels were performed at Cambridge Biomedical, Inc. (Boston, Mass.) as a clinical test and a trough concentration >99 ug/mL was considered therapeutic. Levels were reported with a turnaround time of 4-10 days and were often not immediately available, so dosing adjustment varied as follows: if a trough level was reported prior to the next weekly dose and was therapeutic, the dose was given according to the schedule in FIG. 10. If the patient was due for the next weekly dose and the eculizumab trough concentration was reported and was sub-therapeutic, the subsequent dose was increased by 300 mg/dose. If a sub-therapeutic result was reported 4-5 days after the prior dose, an additional mid-week dose was given. If results were not available for dose adjustment, the same eculizumab induction dose was continued weekly until the trough eculizumab concentration was documented to be above the therapeutic level.

Induction therapy was continued until patients achieved a hematologic response and had documented therapeutic eculizumab levels, at which point a maintenance schedule was started (FIG. 10). Patients had to demonstrate a normalization of hematologic parameters and an improvement in renal parameters to consider stopping eculizumab.

Results

All six patients initially reported significant HSCT-TMA related complications. Patients five and six were critically ill with multi-system organ failure prior to initiation of eculizumab.

The median patient age was 5 years (range 2.4-10.9 years). HSCT-TMA was diagnosed within 100 days (range 6-69 days) of transplant in five patients. One patient was diagnosed one year post transplant after presenting with acute HSCT-TMA and renal failure requiring hemodialysis. At diagnosis of HSCT-TMA all patients had impaired renal function with a median serum cystatin C-eGFR of 18.5 mL/min (range 15-48 mL/min) and nephrotic range proteinuria with median random urine protein/creatinine ratio 11 mg/mg (range 4.5-81.6 mg/mg). Two patients required renal replacement therapy. All patients had severe hypertension requiring six to nine antihypertensive medications at initiation of eculizumab therapy. ADAMTS13 activity level was normal (>67%) in all patients, ruling out TTP.

Terminal complement complex activity (sC5b-9) was elevated in four of five tested patients. The patient with a normal sC5b-9 level was receiving therapeutic plasma exchange (TPE) when the blood sample was obtained and was shown to have elevated sC5b-9 on the sample that was in repository while not on TPE. CFH autoantibody was not detected in any of the patients. Two patients had decreased C4 levels, and one decreased CFH levels. All patients had detectable CFHR1 protein, ruling out a homozygous deletion of CFHR3-CFHR1. One of three tested patients had a heterozygous CFHR3-CFHR1 deletion. Renal biopsy performed on patient two showed severe TMA with diffuse C4d staining in affected arterioles. Patient six had renal TMA confirmed on autopsy.

Clinical Response to Eculizumab

Patients 1-4 had complete clinical responses to eculizumab after achieving therapeutic eculizumab levels. A median of 7 doses (range 4-13 doses) of eculizumab were required to resolve HSCT-TMA. A hematologic response was observed a median of 28.5 days (range 15-45 days) after initiation of eculizumab. All the responders had a dramatic improvement in hypertension with a reduction in the number of antihypertensive medications from 6-9 at the start of eculizumab therapy to 0-2 medications at eculizumab therapy completion. The median time for complete response of all HSCT-TMA parameters, including doubling in cystatin C-eGFR and improvement of proteinuria below 2 mg/mg was 69.5 days (range 29-141 days) after eculizumab initiation. All responders are currently doing well at a median of 38.5 weeks (range 29-63 weeks) post-HSCT-TMA. Patients one and four completely recovered renal function as evidenced by normal cystatin C-eGFR >100 ml/min and the absence of proteinuria and hypertension. Patients two and three, who both had prolonged severe kidney injury due to HSCT-TMA at the start of eculizumab therapy, remain with chronic kidney disease and a cystatin C-eGFR <50 ml/min, but are off hemodialysis and normotensive on losartan therapy.

Patients five and six died with multi-system organ failure and active HSCT-TMA despite eculizumab therapy. Both patients were critically ill with severe kidney injury at the time of starting eculizumab therapy and neither achieved sustained therapeutic eculizumab trough levels or complement blockade, measured by CH50 (see below). All six patients tolerated eculizumab therapy without any attributable side effects or reactions, and there were no meningococcal infections or other bacterial infections.

Eculizumab Pharmacokinetics

Figure 9:
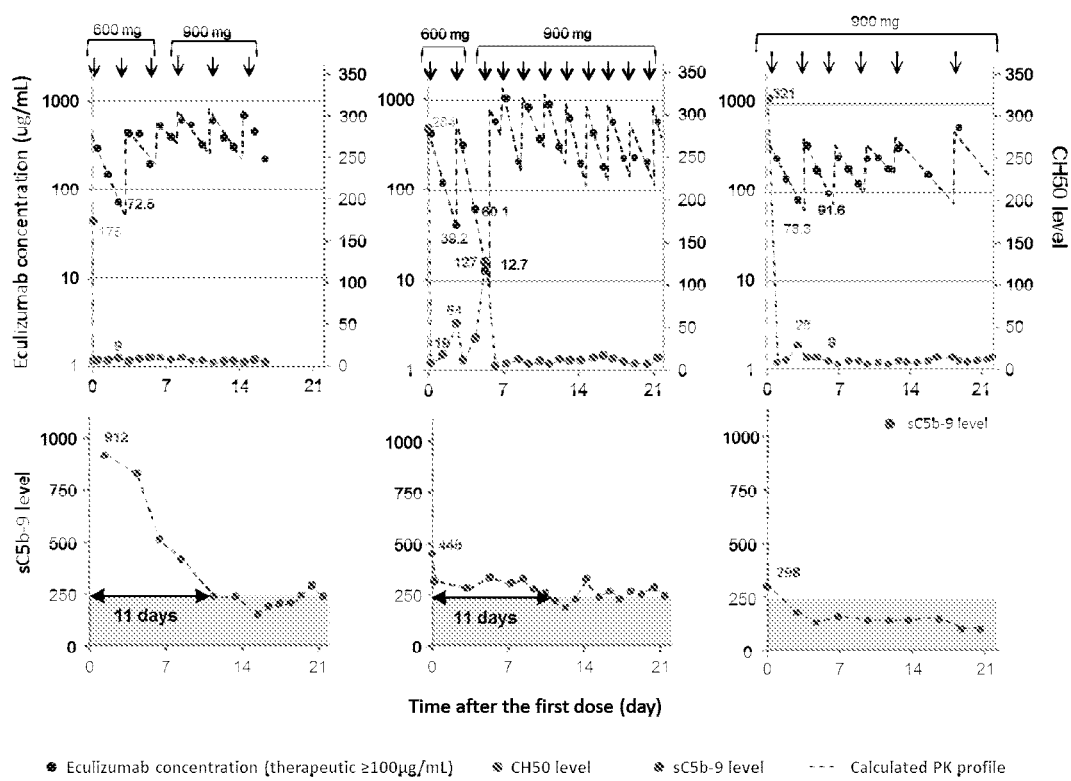
FIG. 9 depicts terminal complement blockage by eculizumab. Representative analyses from of pharmacokinetic and pharmacodynamic eculizumab monitoring during the first 3 weeks of treatment are presented in this figure. The top left and right y axes show eculizumab concentrations and total complement activity (CH50) levels, respectively, using the enzyme immunoassay. Bottom y axis shows sCSb-9 level. The x axis shows time as days from the start of eculizumab therapy with the first eculizumab dose given on day 1. Dosage (mg) and the timing of administration are indicated with arrows on the top of each figure. Blue circles represent observed eculizumab concentrations. Actual measured values are noted beside the circles only when eculizumab concentration if below 99 µg/mL. Blue dashed lines represent predicted eculizumab pharmacokinetic profiles based on a 1-compartment analysis. Red circles represent the CH50 level measured by a hemolytic assay. The actual values are listed on the graph only when the CH50 level is above 15 CH50 units. Green circles represent serum sCSb-9 levels (normal 72-244 ng/mL, shaded area). Elevated sCSb-9 level indicates activated terminal complement. The figure shows that time to sC5b-9 normalization with serum eculizumab level >99 mg/mL depends on the elevation of sC5b-9 at the start of therapy: Patient 1 and 2 with sC5b-9 elevation above 2 times normal (>488 ng/mL) took 11 days to normalize sC5b-9 while patient 3 with sC5b-9 <488 required 4 days.

Representative samples of eculizumab dosing and levels for the first three weeks of therapy are shown in FIG. 9. Overall, four of six patients had sub-therapeutic eculizumab levels after the first dose. Notably, the first eculizumab dose for patient three was higher (600 mg) than recommended (300 mg) for his weight of 9 kg, producing a therapeutic level after the first dose. Therapeutic trough levels of eculizumab >99 µg/mL were eventually achieved in all four responders (patients one though four) using either extra doses or doses that were higher than currently recommended. Eculizumab trough levels remained sub-therapeutic in the two non-responding cases (patients five and six). Patient five did not achieve a therapeutic trough level during five weeks of therapy, despite significant dose escalation to 900 mg twice weekly, starting day on day 24 of therapy. Patient six received two weekly induction doses of 900 mg, as recommended for his weight, before he died without achieving therapeutic eculizumab levels. In both non-responders the eculizumab level was below therapeutic three days after the first dose, but serum eculizumab concentration results were pending so dosing could not be adjusted in a timely manner. Elimination rate constants and systemic clearance of eculizumab showed significant variability among patients, with most rapid clearance in patients five and six who were most ill at the time of treatment, and perhaps more highly catabolic than the responding patients (data not shown).

Relationship between Eculizumab Levels and CH50

Eculizumab and CH50 levels were measured at the same time points and were strongly correlated with each other (FIG. 6-7). Specifically, a CH50 count of 0-3 CAE units corresponded with an eculizumab concentration of >99 µg/mL, except for one measurement from patient six, drawn during an extremely rapid elimination phase in the first week. Conversely, at all sampling time points with a CH50 count of ≥4 CAE units, the patients' eculizumab concentrations were sub-therapeutic at ≤99 µg/mL (p=0.0001).

Complete blockade of complement activity (CH50<3 CAE units) was achieved in all four responders (patients one though four) after the second dose of therapy. Complement blockade was incomplete in the two non-responding cases (patients five and six).

To date, Applicant prescribed eculizumab for 18 patients with high-risk HSCT-TMA (age 2.4-30 years old); 3 patients are still receiving therapy. Out of the other 15 patients, 10 patients (66.7%) were able to resolve HSCT-TMA and 5 died of HSCT complications with active HSCT-TMA. This extended patient cohort supports initial observation that HSCT patients require pharmacodynamically monitored dosing of complement blockade to maintain steady therapeutic levels and all patients require more intense eculizumab dosing than recommended for other diseases. The CH50 level continues to be a very accurate and rapid laboratory test to optimize eculizumab dosing and sC5b-9 measurements indicate when clinical response should be expected. All patients who died with active HSCT-TMA were not able to achieve therapeutic eculizumab dosing even with dose escalation. Overall response rate to therapy remains at 66.7% in this extended cohort of patients. Of note, one of the patients currently on therapy has achieved normalization of sC5b-9 with personalized eculizumab dosing, but remains with active hematologic and renal HSCT-TMA signs and has an elevated C3a level. This demonstrates that some patients may require complement blockade higher in the complement cascade (i.e. at the level of C3) with future agents in addition to or in place of eculizumab.

Discussion

Applicant reports the use of the terminal complement inhibitor, eculizumab, in the treatment of severe HSCT-TMA. Applicant observed that 66.7% of patients had complete resolution of severe HSCT-TMA after achieving therapeutic eculizumab levels. In Applicant's prospective HSCT-TMA study, survival of such patients with high risk HSCT-TMA was 20% without complement blocking therapy. Non-responding patients died without achieving therapeutic drug levels or complement blockade, despite dose escalation. All patients with HSCT-TMA required higher eculizumab dosing and/or more frequent administrations to reach and maintain therapeutic eculizumab levels compared to the dosing regimen currently recommended for patients with aHUS. Earlier or more aggressive therapy, using timely dose escalation might have allowed treatment to be more effective for the non-responding patients. Importantly, Applicant observed that clinical response and eculizumab drug levels correlated well with the total complement activity (CH50), an easily measured pharmacodynamic marker of complement blockade. Measurement of eculizumab serum concentration is not widely available and results may take >1 week to return. Therefore, CH50 testing offers a more rapid assessment of complement blockade and correlation with therapeutic eculizumab level, allowing for practical dose adjustments in a more timely fashion.

Eculizumab pharmacokinetics were analyzed based on a one compartment model. However, the elimination rate constant was not constant after every treatment but decreased over time and stabilized as declining slope of log-transformed eculizumab concentrations, which became shallower after multiple treatments. Thirteen of 18 patients (72%) showed eculizumab concentrations <99 µg/mL 3-4 days after the first eculizumab dose. CH50 suppression was inadequate and was associated with a sub-therapeutic eculizumab level of <99 µg/mL identifying the need for additional treatment in these patients. Conversely, an adequate CH50 suppression was strongly correlated with a therapeutic eculizumab level >99 µg/mL and clinical response, indicating successful complement blockade and adequate drug dosing.

Applicant's study provides important data regarding the time to clinical response to eculizumab in patients with HSCT-TMA. The fastest and most complete response was achieved in patients who started eculizumab therapy promptly after the diagnosis of HSCT-TMA and achieved steady therapeutic eculizumab levels. However, we were able to achieve a hematologic response and control of hypertension even in patients with a prolonged course of HSCT-TMA that had been refractory to therapeutic plasma exchange. In cases with prolonged HSCT-TMA prior to eculizumab therapy, renal recovery was incomplete and the time to recovery was longer, suggesting that the early use of eculizumab may maximize benefit in cases of severe HSCT-TMA.

Based on our observations, at least four to six weeks of therapy with a documented therapeutic eculizumab trough level or adequate complement blockade documented by an undetectable CH50 level before a patient is deemed to be a non-responder may be used. If a patient is determined to be a rapid eliminator after first dose (i.e. 3-4 days after therapy initiation), an additional eculizumab induction dose should be considered to achieve a therapeutic trough level as quickly as possible. An another option would be to increase the first eculizumab dose by 300 mg above the currently recommended first induction dose, especially in critically ill patients who may be highly catabolic. While patients with paroxysmal nocturnal hemoglobinuria (PNH) and aHUS are often committed to life-long therapy with eculizumab, Applicant was able to stop eculizumab therapy in all responders after achieving a hematologic and renal response. The shortest successful course was 4 weeks and the longest therapy was 15 weeks. There were no recurrences of HSCT-TMA in responders after stopping therapy.

All tested patients in the cohort had elevated sCSb-9 levels, documenting an activated terminal complement pathway. Recently we showed that both alternative and classical pathway dysregulation can be observed in HSCT-TMA. Fortunately, complement activated by either the alternative or classical pathway can be blocked by the terminal complement blocker eculizumab making this medication an appropriate therapy regardless of the complement pathway involved in pathogenesis is HSCT-TMA. In conclusion, eculizumab is a promising therapeutic option for HSCT-TMA patients who are at high risk of death. Early therapy initiation may prevent irreversible organ damage, and toxicity is low. Eculizumab dosing in patients with HSCT-TMA should be guided by pharmacokinetic or pharmacodynamic testing, and more aggressive dosing schedules need to be explored in the most ill and catabolic patients. CH50 may serve as an accurate and readily available pharmacodynamic marker of complement blockade, allowing prompt dosage adjustment, perhaps without need for drug level monitoring.

REFERENCES

1. George J N, Li X, McMinn J R, Terrell D R, Vesely S K, Selby G B. Thrombotic thrombocytopenic purpura-hemolytic uremic syndrome following allogeneic HPC transplantation: a diagnostic dilemma Transfusion. 2004; 44:294-304.
2. Kersting S, Koomans H A, Hene R J, Verdonck L F. Acute renal failure after allogeneic myeloablative stem cell transplantation: retrospective analysis of incidence, risk factors and survival. Bone Marrow Transplant. 2007; 39:359-65.
3. Parikh C R, McSweeney P, Schrier R W. Acute renal failure independently predicts mortality after myeloablative allogeneic hematopoietic cell transplant. Kidney Int. 2005; 67:1999-2005.
4. Jodele S, Davies S M, Lane A, Khoury J, Dandoy C, Goebel J, et al. Refined diagnostic and risk criteria for HSCT-associated thrombotic microangiopathy: a prospective study in children and young adults. Blood. 2014, Jul. 24; 124(4):645-53.
5. Keir L, Coward R J. Advances in our understanding of the pathogenesis of glomerular thrombotic microangiopathy. Pediatr Nephroi. 2011; 26:523-33.
6. Waters A M, Licht C. aHUS caused by complement dysregulation: new therapies on the horizon. Pediatr Nephrol. 2011; 26:41-57.
7. Tsai H M. Untying the knot of thrombotic thrombocytopenic purpura and atypical hemolytic uremic syndrome. Am J Med. 2013; 126:200-9.
8. Jodele S, Licht C, Goebel J, Dixon B P, Zhang K, Sivakumaran T A, et al. Abnormalities in the alternative pathway of complement in children with hematopoietic stem cell transplant-associated thrombotic microangiopathy. Blood. 2013; 122:2003-7.
9. Jodele S, Hirsch R, Laskin B, Davies S, Witte D, Chima R. Pulmonary arterial hypertension in pediatric patients with hematopoietic stem cell transplant-associated thrombotic microangiopathy. Biol Blood Marrow Transplant. 2013; 19:202-7.
10. Lerner D, Dandoy C, Hirsch R, Laskin B, Davies S M, Jodele S. Pericardial effusion in pediatric SCT recipients with thrombotic microangiopathy. Bone Marrow Transplant. 2014:June; 49(6):862-3.
11. Inamoto Y, Ito M, Suzuki R, Nishida T, Iida H, Kohno A, et al. Clinicopathological manifestations and treatment of intestinal transplant-associated microangiopathy. Bone Marrow Transplant. 2009; 44:43-9.
12. Glezerman I G, Jhaveri K D, Watson T H, Edwards A M, Papadopoulos E B, Young J W, et al. Chronic kidney disease, thrombotic microangiopathy, and hypertension following T cell-depleted hematopoietic stem cell transplantation. Biol Blood Marrow Transplant. 2010; 16:976-84.
13. Hoffmeister P A, Hingorani S R, Storer B E, Baker K S, Sanders J E. Hypertension in long-term survivors of pediatric hematopoietic cell transplantation. Biol Blood Marrow Transplant. 2010; 16:515-24.
14. Laskin B L, Nehus E, Goebel J, Khoury J C, Davies S M, Jodele S. Cystatin C-estimated glomerular filtration rate in pediatric autologous hematopoietic stem cell transplantation. Biol Blood Marrow Transplant. 2012; 18:1745-52.
15. Laskin B L, Goebel J, Davies S M, Khoury J C, Bleesing J J, Mehta P A, et al. Early clinical indicators of transplant-associated thrombotic microangiopathy in pediatric neuroblastoma patients undergoing auto-SCT. Bone Marrow Transplant. 2011; 46:682-9.
16. Schwartz G J, Furth S L. Glomerular filtration rate measurement and estimation in chronic kidney disease. Pediatr Nephrol. 2007; 22:1839-48.
17. Jodele S, Fukuda T, Vinks A, Mizuno K, Laskin B L, Goebel J, et al. Eculizumab Therapy in Children with Severe Hematopoietic Stem Cell Transplantation-Associated Thrombotic Microangiopathy. Biol Blood Marrow Transplant. 2013:April; 20(4):518-25.
18. Inker L A, Schmid C H, Tighiouart H, Eckfeldt J H, Feldman H I, Greene T, et al. Estimating glomerular filtration rate from serum creatinine and cystatin C. N Engl J Med. 2012; 367:20-9.
19. Nehus E J, Laskin B L, Kathman T I, Bissler J J. Performance of cystatin C-based equations in a pediatric cohort at high risk of kidney injury. Pediatr Nephrol. 2013; 28:453-61.
20. Hingorani S, Gooley T, Pao E, Sandmaier B, McDonald G. Urinary cytokines after HCT: evidence for renal inflammation in the pathogenesis of proteinuria and kidney disease. Bone Marrow Transplant. 2014; 49:403-9.
21. Hingorani S R, Seidel K, Lindner A, Aneja T, Schoch G, McDonald G. Albuminuria in hematopoietic cell transplantation patients: prevalence, clinical associations, and impact on survival. Biol Blood Marrow Transplant. 2008; 14:1365-72.
22. Laskin B L, Goebel J, Davies S M, Jodele S. Small vessels, big trouble in the kidneys and beyond: hematopoietic stem cell transplantation-associated thrombotic microangiopathy. Blood. 2011; 118:1452-62.
23. The fourth report on the diagnosis, evaluation, and treatment of high blood pressure in children and adolescents. Pediatrics. 2004; 114:555-76.
24. Goodwin J E, Geller D S. Glucocorticoid-induced hypertension. Pediatr Nephrol. 2012; 27:1059-66.

25. Moulder J E, Cohen E P, Fish B L. Captopril and losartan for mitigation of renal injury caused by single-dose total-body irradiation. Radiation research. 2011; 175:29-36.
26. Hingorani S. Chronic kidney disease after liver, cardiac, lung, heart-lung, and hematopoietic stem cell transplant. Pediatr Nephrol. 2008; 23:879-88.
27. Haines H L, Laskin B L, Goebel J, Davies S M, Yin H J, Lawrence J, et al. Blood, and not urine, BK viral load predicts renal outcome in children with hemorrhagic cystitis following hematopoietic stem cell transplantation. Biol Blood Marrow Transplant. 2011; 17:1512-9.
28. O'Donnell P H, Swanson K, Josephson M A, Artz A S, Parsad S D, Ramaprasad C, et al. B K virus infection is associated with hematuria and renal impairment in recipients of allogeneic hematopoetic stem cell transplants. Biol Blood Marrow Transplant. 2009; 15:1038-48 el.
29. Laskin B L, Maisel J, Goebel J, Yin H J, Luo G, Khoury J C, et al. Renal Arteriolar C4d Deposition: A Novel Characteristic of Hematopoietic Stem Cell Transplantation-Associated Thrombotic Microangiopathy. Transplantation. 2013:Jul. 27; 96(2):217-23.
30. Dandoy C E, Hirsch R, Chima R, Davies S M, Jodele S. Pulmonary hypertension after hematopoietic stem cell transplantation. Biol Blood Marrow Transplant. 2013; 19:1546-56.
31. Houtchens J, Martin D, Klinger J R. Diagnosis and management of pulmonary arterial hypertension Pulmonary medicine. 2011; 2011:845864.
32. Perkowska-Ptasinska A, Sulikowska-Rowinska A, Pazik J, Komuda-Leszek E, Durlik M. Thrombotic nephropathy and pulmonary hypertension following autologous bone marrow transplantation in a patient with acute lymphoblastic leukemia: case report. Transplant Proc. 2006; 38:295-6.
33. Rabinovitch M. Molecular pathogenesis of pulmonary arterial hypertension. The Journal of clinical investigation. 2012; 122:4306-13.
34. Milan A, Magnino C, Veglio F. Echocardiographic indexes for the non-invasive evaluation of pulmonary hemodynamics. Journal of the American Society of Echocardiography: official publication of the American Society of Echocardiography. 2010; 23:225-39; quiz 332-4.
35. Galie N, Hoeper M M, Humbert M, Torbicki A, Vachiery J L, Barbera J A, et al. Guidelines for the diagnosis and treatment of pulmonary hypertension: the Task Force for the Diagnosis and Treatment of Pulmonary Hypertension of the European Society of Cardiology (ESC) and the European Respiratory Society (ERS), endorsed by the International Society of Heart and Lung Transplantation (ISHLT). European heart journal. 2009; 30:2493-537.
36. Aldoss O, Gruenstein D H, Bass J L, Steinberger J, Zhang Y, Defor T E, et al. Pericardial effusion after pediatric hematopoietic cell transplant. Pediatr Transplant. 2013; 17:294-9.
37. Norkin M, Ratanatharathorn V, Ayash L, Abidi M H, Al-Kadhimi Z, Lum L G, et al. Large pericardial effusion as a complication in adults undergoing SCT. Bone Marrow Transplant. 2011; 46:1353-6.
38. Mohammed J, Filler G, Price A, Sharma A P. Cardiac tamponade in diarrhoea-positive haemolytic uraemic syndrome. Nephrol Dial Transplant. 2009; 24:679-81.
39. Sagrista-Sauleda J, Merce A S, Soler-Soler J. Diagnosis and management of pericardial effusion. World journal of cardiology. 2011; 3:135-43.
40. Aljitawi O S, Rodriguez L, Madan R, Ganguly S, Abhyankar S, McGuirk J P. Late-onset intestinal perforation in the setting of posttransplantation microangiopathy: a case report. Transplant Proc. 2010; 42:3892-3.
41. Hewamana S, Austen B, Murray J, Johnson S, Wilson K. Intestinal perforation secondary to haematopoietic stem cell transplant associated thrombotic microangiopathy. Eur J Haematol. 2009; 83:277.
42. Narimatsu H, Kami M, Hara S, Matsumura T, Miyakoshi S, Kusumi E, et al. Intestinal thrombotic microangiopathy following reduced-intensity umbilical cord blood transplantation. Bone Marrow Transplant. 2005; 36:517-23.
43. Nishida T, Hamaguchi M, Hirabayashi N, Haneda M, Terakura S, Atsuta Y, et al. Intestinal thrombotic microangiopathy after allogeneic bone marrow transplantation: a clinical imitator of acute enteric graft-versus-host disease. Bone Marrow Transplant. 2004; 33:1143-50.
44. Yamada-Fujiwara M, Miyamura K, Fujiwara T, Tohmiya Y, Endo K, Onishi Y, et al. Diagnosis of intestinal graft-versus-host disease and thrombotic microangiopathy after allogeneic stem cell transplantation. The Tohoku journal of experimental medicine. 2012; 227:31-7.
45. Fujino M, Kim Y, Ito M. Intestinal thrombotic microangiopathy induced by FK506 in rats. Bone Marrow Transplant. 2007; 39:367-72.
46. Piscitelli D, Fiore M G, Rossi R, Casiello M, Sanguedolce F. Unusual case report of thrombotic microangiopathy of the small bowel following liver transplantation, a possible immunosuppressant-induced disease with histological and ultrastructural findings. TheScientificWorldJournal. 2009; 9:1031-4.
47. Dierickx D, Monbaliu D, De Rycke A, Wisanto E, Lerut E, Devos T, et al. Thrombotic microangiopathy following intestinal transplantation: a single center experience. Transplant Proc. 2010; 42:79-81.
48. Martinez M T, Bucher C, Stussi G, Heim D, Buser A, Tsakiris D A, et al. Transplant-associated microangiopathy (TAM) in recipients of allogeneic hematopoietic stem cell transplants. Bone Marrow Transplant. 2005; 36:993-1000.
49. Fuge R, Bird J M, Fraser A, Hart D, Hunt L, Cornish J M, et al. The clinical features, risk factors and outcome of thrombotic thrombocytopenic purpura occurring after bone marrow transplantation. Br J Haematol. 2001; 113: 58-64.
50. Staykov D, Schwab S. Posterior reversible encephalopathy syndrome. Journal of intensive care medicine. 2012; 27:11-24.
51. Roth C, Ferbert A. The posterior reversible encephalopathy syndrome: what's certain, what's new? Practical neurology. 2011; 11:136-44.
52. Ishikawa Y, Nishio S, Sasaki H, Kudo R, Goto H, Ito M, et al. Transplantation-associated thrombotic microangiopathy after steroid pulse therapy for polyserositis related to graft-versus-host disease. Clin Exp Nephrol. 2011; 15:179-83.
53. Batts E D, Lazarus H M. Diagnosis and treatment of transplantation-associated thrombotic microangiopathy: real progress or are we still waiting? Bone Marrow Transplant. 2007; 40:709-19.
54. Kojouri K, George J N. Thrombotic microangiopathy following allogeneic hematopoietic stem cell transplantation. Curr Opin Oncol. 2007; 19:148-54.
55. Nakamae H, Yamane T, Hasegawa T, Nakamae M, Terada Y, Hagihara K, et al. Risk factor analysis for thrombotic microangiopathy after reduced-intensity or myeloablative allogeneic hematopoietic stem cell transplantation. Am J Hematol. 2006; 81:525-31.

56. Hale G A, Bowman L C, Rochester R J, Benaim E, Heslop H E, Krance R A, et al. Hemolytic uremic syndrome after bone marrow transplantation: clinical characteristics and outcome in children. Biol Blood Marrow Transplant. 2005; 11:912-20.
57. Worel N, Greinix H T, Leitner G, Mitterbauer M, Rabitsch W, Rosenmayr A, et al. ABO-incompatible allogeneic hematopoietic stem cell transplantation following reduced-intensity conditioning: close association with transplant-associated microangiopathy. Transfus Apher Sci. 2007; 36:297-304.
58. Willems E, Baron F, Seidel L, Frere P, Fillet G, Beguin Y. Comparison of thrombotic microangiopathy after allogeneic hematopoietic cell transplantation with high-dose or nonmyeloablative conditioning. Bone Marrow Transplant. 2010; 45:689-93.
59. Rosenthal J, Pawlowska A, Bolotin E, Cervantes C, Maroongroge S, Thomas S H, et al. Transplant-associated thrombotic microangiopathy in pediatric patients treated with sirolimus and tacrolimus. Pediatr Blood Cancer. 2011; 57:142-6.
60. Rodriguez R, Nakamura R, Palmer J M, Parker P, Shayani S, Nademanee A, et al. A phase II pilot study of tacrolimus/sirolimus GVHD prophylaxis for sibling donor hematopoietic stem cell transplantation using 3 conditioning regimens. Blood. 2010; 115:1098-105.
61. Cutler C, Henry N L, Magee C, Li S, Kim H T, Alyea E, et al. Sirolimus and thrombotic microangiopathy after allogeneic hematopoietic stem cell transplantation. Biol Blood Marrow Transplant. 2005; 11:551-7.
62. Platzbecker U, von Bonin M, Goekkurt E, Radke J, Binder M, Kiani A, et al. Graft-versus-host disease prophylaxis with everolimus and tacrolimus is associated with a high incidence of sinusoidal obstruction syndrome and microangiopathy: results of the EVTAC trial. Biol Blood Marrow Transplant. 2009; 15:101-8.
63. Changsirikulchai S, Myerson D, Guthrie K A, McDonald G B, Alpers C E, Hingorani S R. Renal thrombotic microangiopathy after hematopoietic cell transplant: role of GVHD in pathogenesis. Clin J Am Soc Nephrol. 2009; 4:345-53.
64. Tichelli A, Gratwohl A. Vascular endothelium as 'novel' target of graft-versus-host disease. Best Pract Res Clin Haematol. 2008; 21:139-48.
65. Cooke K R, Jannin A, Ho V. The contribution of endothelial activation and injury to end-organ toxicity following allogeneic hematopoietic stem cell transplantation. Biol Blood Marrow Transplant. 2008; 14:23-32.
66. Biedermann B C. Vascular endothelium and graft-versus-host disease. Best Pract Res Clin Haematol. 2008; 21:129-38.
67. Takatsuka H, Takemoto Y, Yamada S, Wada H, Tamura S, Fujimori Y, et al. Complications after bone marrow transplantation are manifestations of systemic inflammatory response syndrome. Bone Marrow Transplant. 2000; 26:419-26.
68. Nakamura Y, Yujiri T, Ando T, Hisano S, Tanizawa Y. Nephrotic syndrome associated with thrombotic microangiopathy following allogeneic stem-cell transplantation for myelodysplastic syndrome. Br J Haematol. 2007; 136:857-9; author reply 9-60.
69. Cho B S, Min C K, Eom K S, Kim Y J, Kim H J, Lee S, et al. Clinical impact of thrombotic microangiopathy on the outcome of patients with acute graft-versus-host disease after allogeneic hematopoietic stem cell transplantation. Bone Marrow Transplant. 2008; 41:813-20.
70. Chang A, Hingorani S, Kowalewska J, Flowers M E, Aneja T, Smith K D, et al. Spectrum of renal pathology in hematopoietic cell transplantation: a series of 20 patients and review of the literature. Clin J Am Soc Nephrol. 2007; 2:1014-23.
71. Lopes da Silva R, Ferreira I, Teixeira G, Cordeiro D, Mafra M, Costa I, et al. BK virus encephalitis with thrombotic microangiopathy in an allogeneic hematopoietic stem cell transplant recipient. Transpl Infect Dis. 2011; 13:161-7.
72. Uderzo C, Bonanomi S, Busca A, Renoldi M, Ferrari P, Iacobelli M, et al. Risk factors and severe outcome in thrombotic microangiopathy after allogeneic hematopoietic stem cell transplantation. Transplantation. 2006; 82:638-44.
73. Schwimmer J, Nadasdy T A, Spitalnik P F, Kaplan K L, Zand M S. De novo thrombotic microangiopathy in renal transplant recipients: a comparison of hemolytic uremic syndrome with localized renal thrombotic microangiopathy. Am J Kidney Dis. 2003; 41:471-9.
74. Labrador J, Lopez-Corral L, Lopez-Godino O, Vazquez L, Cabrero-Calvo M, Perez-Lopez R, et al. Risk factors for thrombotic microangiopathy in allogeneic hematopoietic stem cell recipients receiving GVHD prophylaxis with tacrolimus plus MTX or sirolimus. Bone Marrow Transplant. 2014:May; 49(5):684-90.
75. Shayani S, Palmer J, Stiller T, Liu X, Thomas S H, Khuu T, et al. Thrombotic microangiopathy associated with sirolimus level after allogeneic hematopoietic cell transplantation with tacrolimus/sirolimus-based graft-versus-host disease prophylaxis. Biol Blood Marrow Transplant. 2013; 19:298-304.
76. Siami K, Kojouri K, Swisher K K, Selby G B, George J N, Laszik Z G. Thrombotic microangiopathy after allogeneic hematopoietic stem cell transplantation: an autopsy study. Transplantation. 2008; 85:22-8.
77. Mii A, Shimizu A, Masuda Y, Fujino T, Kaneko T, Utsumi K, et al. Renal thrombotic microangiopathy associated with chronic humoral graft versus host disease after hematopoietic stem cell transplantation. Pathol Int. 2011; 61:34-41.
78. Mii A, Shimizu A, Kaneko T, Fujita E, Fukui M, Fujino T, et al. Renal thrombotic microangiopathy associated with chronic graft-versus-host disease after allogeneic hematopoietic stem cell transplantation. Pathol Int. 2011; 61:518-27.
79. Sadeghi B, Al-Chaqmaqchi H, Al-Hashmi S, Brodin D, Hassan Z, Abedi-Valugerdi M, et al. Early-phase GVHD gene expression profile in target versus non-target tissues: kidney, a possible target? Bone Marrow Transplant. 2013; 48:284-93.
80. Brukamp K, Doyle A M, Bloom R D, Bunin N, Tomaszewski J E, Cizman B. Nephrotic syndrome after hematopoietic cell transplantation: do glomerular lesions represent renal graft-versus-host disease? Clin J Am Soc Nephrol. 2006; 1:685-94.
81. Ho V T, Cutler C, Carter S, Martin P, Adams R, Horowitz M, et al. Blood and marrow transplant clinical trials network toxicity committee consensus summary: thrombotic microangiopathy after hematopoietic stem cell transplantation. Biol Blood Marrow Transplant. 2005; 11:571-5.
82. Ruutu T, Barosi G, Benjamin R J, Clark R E, George J N, Gratwohl A, et al. Diagnostic criteria for hematopoietic stem cell transplant-associated microangiopathy: results of a consensus process by an International Working Group. Haematologica. 2007; 92:95-100.

83. Cho B S, Yahng S A, Lee S E, Eom K S, Kim Y J, Kim H J, et al. Validation of recently proposed consensus criteria for thrombotic microangiopathy after allogeneic hematopoietic stem-cell transplantation. Transplantation. 2010; 90:918-26.
84. van der Plas R M, Schiphorst M E, Huizinga E G, Hene R J, Verdonck L F, Sixma J J, et al. von Willebrand factor proteolysis is deficient in classic, but not in bone marrow transplantation-associated, thrombotic thrombocytopenic purpura. Blood. 1999; 93:3798-802.
85. Peyvandi F, Siboni S M, Lambertenghi Deliliers D, Lavoretano S, De Fazio N, Moroni B, et al. Prospective study on the behaviour of the metalloprotease ADAMTS13 and of von Willebrand factor after bone marrow transplantation. Br J Haematol. 2006; 134:187-95.
86. Carreras E, Diaz-Ricart M. The role of the endothelium in the short-term complications of hematopoietic SCT. Bone Marrow Transplant. 2011; 46:1495-502.
87. Holmes L V, Strain L, Staniforth S J, Moore I, Marchbank K, Kavanagh D, et al. Determining the population frequency of the CFHR3/CFHR1 deletion at 1q32. PloS one. 2013; 8:e60352.
88. Legendre C M, Licht C, Loirat C. Eculizumab in atypical hemolytic-uremic syndrome. N Engl J Med. 2013; 369: 1379-80.
89. Tati R, Kristoffersson A C, Stahl A L, Rebetz J, Wang L, Licht C, et al. Complement activation associated with ADAMTS13 deficiency in human and murine thrombotic microangiopathy. J Immunol. 2013; 191:2184-93.
90. Reti M, Farkas P, Csuka D, Razso K, Schlammadinger A, Udvardy M L, et al. Complement activation in thrombotic thrombocytopenic purpura. Journal of thrombosis and haemostasis: JTH. 2012; 10:791-8.
91. Cataland S R, Holers V M, Geyer S, Yang S, Wu H M. Biomarkers of the alternative pathway and terminal complement activity at presentation confirms the clinical diagnosis of aHUS and differentiates aHUS from TTP. Blood. 2014, Jun. 12; 123(24):3733-8.
92. Orth D, Khan A B, Naim A, Grif K, Brockmeyer J, Karch H, et al. Shiga toxin activates complement and binds factor H: evidence for an active role of complement in hemolytic uremic syndrome. J Immunol. 2009; 182:6394-400.
93. Thurman J M, Marians R, Emlen W, Wood S, Smith C, Akana H, et al. Alternative pathway of complement in children with diarrhea-associated hemolytic uremic syndrome. Clin J Am Soc Nephrol. 2009; 4:1920-4.
94. Lapeyraque A L, Malina M, Fremeaux-Bacchi V, Boppel T, Kirschfink M, Oualha M, et al. Eculizumab in severe Shiga-toxin-associated HUS. N Engl J Med. 2011; 364: 2561-3.
95. Menne J, Nitschke M, Stingele R, Abu-Tair M, Beneke J, Bramstedt J, et al. Validation of treatment strategies for enterohaemorrhagic *Escherichia coli* O104:H4 induced haemolytic uraemic syndrome: case-control study. BMJ. 2012; 345:e4565.
96. Kielstein J T, Beutel G, Fleig S, Steinhoff J, Meyer T N, Hafer C, et al. Best supportive care and therapeutic plasma exchange with or without eculizumab in Shiga-toxin-producing *E. coli* O104:H4 induced haemolytic-uraemic syndrome: an analysis of the German STEC-HUS registry. Nephrol Dial Transplant. 2012; 27:3807-15.
97. Noris M, Mescia F, Remuzzi G. STEC-HUS, atypical HUS and TTP are all diseases of complement activation. Nature reviews Nephrology. 2012; 8:622-33.
98. Song D, Wu L H, Wang F M, Yang X W, Zhu D, Chen M, et al. The spectrum of renal thrombotic microangiopathy in lupus nephritis. Arthritis research & therapy. 2013; 15:R12.
99. Crovetto F, Borsa N, Acaia B, Nishimura C, Frees K, Smith R J, et al. The genetics of the alternative pathway of complement in the pathogenesis of HELLP syndrome. The journal of maternal-fetal & neonatal medicine: the official journal of the European Association of Perinatal Medicine, the Federation of Asia and Oceania Perinatal Societies, the International Society of Perinatal Obstet. 2012; 25:2322-5.
100. Totina A, Iorember F, El-Dahr S S, Yosypiv I V. Atypical hemolytic-uremic syndrome in a child presenting with malignant hypertension. Clinical pediatrics. 2013; 52:183-6.
101. Nadasdy T. Thrombotic microangiopathy in renal allografts: the diagnostic challenge. Current opinion in organ transplantation. 2014; 19:283-92.
102. Gooley T A, Chien J W, Pergam S A, Hingorani S, Sorror M L, Boeckh M, et al. Reduced mortality after allogeneic hematopoietic-cell transplantation. N Engl J Med. 2010; 363:2091-101.
103. Rajpal J S, Patel N, Vogel R I, Kashtan C E, Smith A R. Improved survival over the last decade in pediatric patients requiring dialysis after hematopoietic cell transplantation. Biol Blood Marrow Transplant. 2013; 19:661-5.
104. Arai Y, Yamashita K, Mizugishi K, Watanabe T, Sakamoto S, Kitano T, et al. Serum neutrophil extracellular trap levels predict thrombotic microangiopathy after allogeneic stem cell transplantation. Biol Blood Marrow Transplant. 2013; 19:1683-9.
105. Jodele S, Laskin B L, Goebel J, Khoury J C, Pinkard S L, Carey P M, et al. Does early initiation of therapeutic plasma exchange improve outcome in pediatric stem cell transplant-associated thrombotic microangiopathy? Transfusion. 2013; 53:661-7.
106. Licht C, Weyersberg A, Heinen S, Stapenhorst L, Devenge J, Beck B, et al. Successful plasma therapy for atypical hemolytic uremic syndrome caused by factor H deficiency owing to a novel mutation in the complement cofactor protein domain 15. Am J Kidney Dis. 2005; 45:415-21.
107. Marr H, McDonald E J, Merriman E, Smith M, Mangos H, Stoddart C, et al. Successful treatment of transplant-associated microangiopathy with rituximab. N Z Med J. 2009; 122:72-4.
108. Carella A M, D'Arena G, Greco M M, Nobile M, Cascavilla N. Rituximab for allo-SCT-associated thrombotic thrombocytopenic purpura. Bone Marrow Transplant. 2008; 41:1063-5.
109. Au W Y, Ma E S, Lee T L, Ha S Y, Fung A T, Lie A K, et al. Successful treatment of thrombotic microangiopathy after haematopoietic stem cell transplantation with rituximab. Br J Haematol. 2007; 137:475-8.
110. Jodele S, Bleesing J J, Mehta P A, Filipovich A H, Laskin B L, Goebel J, et al. Successful early intervention for hyperacute transplant-associated thrombotic microangiopathy following pediatric hematopoietic stem cell transplantation. Pediatr Transplant. 2012; 16:E39-42.
111. Choi C M, Schmaier A H, Snell M R, Lazarus H M. Thrombotic microangiopathy in haematopoietic stem cell transplantation: diagnosis and treatment. Drugs. 2009; 69:183-98.

112. Naina H V, Gertz M A, Elliott M A. Thrombotic microangiopathy during peripheral blood stem cell mobilization. J Clin Apher. 2009; 24:259-61.
113. San T, Moini H, Emerk K, Bilsel S. Protective effect of defibrotide on perfusion induced endothelial damage. Thrombosis research. 2000; 99:335-41.
114. Schroder H. Defibrotide protects endothelial cells, but not L929 tumour cells, from tumour necrosis factor-alpha-mediated cytotoxicity. The Journal of pharmacy and pharmacology. 1995; 47:250-2.
115. Sucak G T, Aki Z S, Yagci M, Yegin Z A, Ozkurt Z N, Haznedar R. Treatment of sinusoidal obstruction syndrome with defibrotide: a single-center experience. Transplant Proc. 2007; 39:1558-63.
116. Chalandon Y, Roosnek E, Mermillod B, Newton A, Ozsahin H, Wacker P, et al. Prevention of veno-occlusive disease with defibrotide after allogeneic stem cell transplantation. Biol Blood Marrow Transplant. 2004; 10:347-54.
117. Carmona A, Diaz-Ricart M, Palomo M, Molina P, Pino M, Rovira M, et al. Distinct deleterious effects of cyclosporine and tacrolimus and combined tacrolimus-sirolimus on endothelial cells: protective effect of defibrotide. Biol Blood Marrow Transplant. 2013; 19:1439-45.
118. Corbacioglu S, Cesaro S, Faraci M, Valteau-Couanet D, Gruhn B, Rovelli A, et al. Defibrotide for prophylaxis of hepatic veno-occlusive disease in paediatric haemopoietic stem-cell transplantation: an open-label, phase 3, randomised controlled trial. Lancet. 2012; 379:1301-9.
119. Uderzo C, Fumagalli M, De Lorenzo P, Busca A, Vassallo E, Bonanomi S, et al. Impact of thrombotic thrombocytopenic purpura on leukemic children undergoing bone marrow transplantation. Bone Marrow Transplant. 2000; 26:1005-9.
120. Eremina V, Jefferson J A, Kowalewska J, Hochster H, Haas M, Weisstuch J, et al. VEGF inhibition and renal thrombotic microangiopathy. N Engl J Med. 2008; 358:1129-36.
121. Noris M, Remuzzi G. Atypical hemolytic-uremic syndrome. N Engl J Med. 2009; 361:1676-87.
122. Colvin R B. Antibody-mediated renal allograft rejection: diagnosis and pathogenesis. J Am Soc Nephrol. 2007; 18:1046-56.
123. Kurniati N F, van Meurs M, Vom Hagen F, Jongman R M, Moser J, Zwiers P J, et al. Pleiotropic effects of angiopoietin-2 deficiency do not protect mice against endotoxin-induced acute kidney injury. Nephrol Dial Transplant. 2013; 28:567-75.
124. Imhof B A, Aurrand-Lions M. Angiogenesis and inflammation face off. Nature medicine. 2006; 12:171-2.
125. Ueda N, Chihara D, Kohno A, Tatekawa S, Ozeki K, Watamoto K, et al. Predictive Value of Circulating Angiopoietin-2 for Endothelial Damage-Related Complications in Allogeneic Hematopoietic Stem Cell Transplantation. Biology of Blood and Marrow Transplantation. 2014; 20:1335-40.
126. Richardson P G, Soiffer R J, Antin J H, Uno H, Jin Z, Kurtzberg J, et al. Defibrotide for the treatment of severe hepatic veno-occlusive disease and multiorgan failure after stem cell transplantation: a multicenter, randomized, dose-finding trial. Biol Blood Marrow Transplant. 2010; 16:1005-17.
127. Wuhl E, Trivelli A, Picca S, Litwin M, Peco-Antic A, Zurowska A, et al. Strict blood-pressure control and progression of renal failure in children. N Engl J Med. 2009; 361:1639-50.
128. Lovric S, Lukasz A, Hafer C, Kielstein J T, Haubitz M, Haller H, et al. Removal of elevated circulating angiopoietin-2 by plasma exchange—a pilot study in critically ill patients with thrombotic microangiopathy and anti-glomerular basement membrane disease. Thrombosis and haemostasis. 2010; 104:1038-43.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Where multiple features/embodiments are disclosed, it is to be understood that one feature/embodiment may be combined with any other feature/embodiment of the disclosure, and that such is within the scope of the invention.

What is claimed is:

1. A method of treating hematopoietic stem cell transplantation associated thrombotic microangiopathy (HSCT-TMA) in an individual that has undergone a bone marrow transplant, comprising
    a) administering a first eculizumab dose to said individual;
    b) performing pharmacokinetic dose monitoring in said individual by measuring one or more of eculizumab levels, complement activity, or complement levels in said individual; and
    c) maintaining a therapeutic eculizumab level of greater than or equal to 99 µg/mL in said individual.

2. The method of claim 1, wherein an eculizumab dose is administered every day, or every two days, or every three days until said eculizumab level of greater than or equal to 99 µg/mL is achieved in said individual.

3. The method of claim 1, wherein said maintaining comprises administering at least one dose, at least two doses, at least three doses, or at least four doses, or more than four doses of eculizumab.

4. The method of claim 1, wherein said pharmacokinetic dose monitoring comprises measuring total complement activity (CH50) to obtain a CH50 measurement, wherein said individual is administered eculizumab until the CH50 measurement obtained from said individual is from about 0 to about 3 CAE units, as measured by enzyme immunoassay, or wherein the CH50 measurement is <15 CH50 units as measured using a hemolytic method using standardized sheep erythrocytes.

5. The method of claim 1, wherein said pharmacokinetic dose monitoring comprises
    a) measuring total complement activity (CH50) prior to said administering of said first eculizumab dose to obtain an initial CH50 measurement; and
    b) measuring total CH50 activity after said administering of said first eculizumab dose to obtain a post-treatment CH50 measurement; and
    wherein said maintaining comprises administering eculizumab until said post-treatment CH50 measurement is from about 0 to about 3 CAE units, as measured by enzyme immunoassay, or wherein the CH50 measurement is <15 CH50 units as measured using a hemolytic method using standardized sheep erythrocytes.

6. The method of claim 5, wherein said maintaining is carried out for a period of time sufficient to resolve HSCT-TMA.

7. The method of claim 5, wherein said maintaining is carried out over a period of about four to about 15 weeks, wherein maintaining of said eculizumab is at a dosage sufficient to reduce CH50 levels to 0-3 CAE units as measured by enzyme immunoassay, or wherein the CH50 measurement is <15 CH50 units as measured using a hemolytic method using standardized sheep erythrocytes.

8. The method of claim 5, wherein said maintaining is carried out over a period of time sufficient to achieve a favorable hematologic response comprising resolution of one or more hematologic TMA markers.

9. The method of claim 8, wherein said maintaining is carried out over a period of time sufficient to achieve a complete response, wherein said complete response comprises normalization of said individual's hematologic parameters.

10. The method of claim 1 or 5, wherein said individual is administered eculizumab weekly.

11. The method of claim 1 or 5, wherein said individual is administered a weekly eculizumab dose, and wherein if said weekly eculizumab dose is not therapeutic, a subsequent weekly eculizumab dose is increased by 300 mg.

12. The method of claim 1 or 5, wherein said maintaining is carried out over a period of time sufficient to achieve a favorable hematologic response, wherein a favorable hematological response comprises one or more of normalization of lactate dehydrogenase (LDH), resolution of need for red cell and platelet transfusions, and disappearance of schistocytes.

13. The method of claim 1 or 5, wherein said maintaining is carried out over a period of time sufficient to achieve a complete response, wherein said complete response comprises normalization of said individual's hematologic parameters, a renal response measured as a doubling of the cystatin C-estimated glomerular filtration rate (eGFR) and improvement of proteinuria to values below the nephrotic range as defined by random spot urine protein to creatinine ratio below 2 mg/mg.

14. The method of claim 1, wherein said first eculizumab dose is based on the weight of said individual.

15. The method of claim 1, wherein when said therapeutic eculizumab level is not achieved, a second dose of eculizumab is administered to said individual at an interval of less than a week.

16. The method of claim 1, wherein if an eculizumab level of less than 99 µg/mL is detected, a second eculizumab dose comprising double the first eculizumab dose is administered to said individual.

17. The method of claim 1, wherein said pharmacokinetic dose monitoring comprises measuring complement activity or complement level in said individual.

* * * * *